United States Patent [19]

Ruoslahti et al.

[11] Patent Number: 5,654,270
[45] Date of Patent: Aug. 5, 1997

[54] USE OF FIBROMODULIN TO PREVENT OR REDUCE DERMAL SCARRING

[75] Inventors: Erkki I. Ruoslahti, Rancho Santa Fe; Michael T. Longaker, San Francisco, both of Calif.; David J. Whitby, Adel, United Kingdom

[73] Assignee: La Jolla Cancer Research Foundation, La Jolla, Calif.

[21] Appl. No.: 303,238

[22] Filed: Sep. 8, 1994

Related U.S. Application Data

[63] Continuation of Ser. No. 978,931, Nov. 17, 1992, abandoned, which is a continuation-in-part of Ser. No. 882,345, May 13, 1992, abandoned, which is a continuation of Ser. No. 792,192, Nov. 14, 1991, abandoned, which is a continuation-in-part of Ser. No. 467,888, Jan. 22, 1990, abandoned, which is a continuation-in-part of Ser. No. 212,702, Jun. 28, 1988, abandoned.

[51] Int. Cl.$^6$ .................... C07K 14/435; A61K 38/17
[52] U.S. Cl. ........................ 514/8; 514/2; 435/69.1
[58] Field of Search ................ 514/2, 8; 435/69.1

[56] References Cited

FOREIGN PATENT DOCUMENTS

| | | |
|---|---|---|
| 282317A2 | 9/1988 | European Pat. Off. . |
| 349480A1 | 1/1990 | European Pat. Off. . |
| WO90/06767 | 6/1990 | WIPO . |
| WO91/10727 | 7/1991 | WIPO . |
| PCT/US92/09871 | 3/1993 | WIPO . |

OTHER PUBLICATIONS

Shah, M., et al. (1991) *J. Cell. Biochem.* 15(suppl. F): 198, abstract No. Q423.
Takeuchi, Y., et al. (1994) *J. Biol. Chem.* 269: 32634–8.
Hausser, H., et al. (1994) *FEBS Lett.* 353: 243–5.
Oldberg, A., et al. (1989) *EMBO J.* 8: 2601–04.
Montesano, R., et al. (1985) *Proc. Natl. Acad. Sci. USA* 85: 4894–97.
Moriyama, K., et al. (1991) *Matrix* 11: 190–96.
Adzick, N. S., et al. (1992) *Ann. Surg.* 215: 3–7.
Lorenz, H. P., et al. (1993) *Western J. Med.* 159: 350–55.
Border et al., "Antagonists of transforming growth factor–β: A novel approach to treatment of glomerulonephritis and prevention of glomerulosclerosis" *Kidney Int.* 41:566–570 (1992).
Sporn, M.B., et al. (1992) *J. Cell Biol.* 119 (2): 1017–21.
Border, W.A., et al. (1992) *J. Clin. Invest.* 90: 1–7.
Castellot et al., "Inhibition of Vascular Smooth Muscle Cell Growth by Endothelial Cell–Derived Heparin" *J. Biol. Chem.* 257:11256–11260 (1982).
Vogel et al., "Specific Inhibition of Type I and Type II collagen Fibrillogenesis by the Small Proteoglycan of Tendon" *Biochem. J.* 223:587–597 (1984).
Massague et al., "Cellular Receptors for Type Beta Transforming Growth Factor" *J. Biol. Chem.* 260:2636–2645 (1985).

Fritze et al., "An Antiproliferative Heparin Sulfate Species Produced by Postconfluent Smooth Muscle Cells" *J. Cell Biol.* 100:1041–1049 (1985).
Krusius et al., "Primary Structure of an Extracellular Matrix Proteoglycan Core Protein Deduced from Cloned cDNA" *Proc. Natl. Acad. Sci. USA* 83:7683–7687 (1986).
Castellot et al., "Glomerular Endothelial Cells Secrete a heparinlike Inhibitor and a Peptide Stimulator of Mesangial Cell Proliferation" *Am. J. Pathol.* 125:493–500 (1986).
Cheifetz et al., "The Transforming Growth Factor–Beta System, a Complex Pattern of Cross–Reactive Ligands and Receptors" *Cell* 48:409–415 (1987).
Ishihara et al., "Involvement of Phosphatidylinositol and Insulin in the Cordinate Regulation of Protecheparan Sulfate Metabolism and Hepatocyte Growth" *J. Biol. Chem.* 262:4706–4716 (1987).
Day et al., "Molecular Cloning and Sequence Analysis of the cDNA for Small Proteoglycan II of Bovine Bone" *Biochem. J.* 248:801–805 (1987).
Patthy, "Detecting Homology of Distantly Related Proteins with Consensus Sequences" *J. Mol. Biol.* 198:567–577 (1987).
Bassols et al., "Transforming Growth Factor Beta Regulates the Expression and Structure of Extracellular Matrix Chondroitin/Dermatan Sulfate Proteoglycans" *J. Biol. Chem.* 263:3039–3045 (1988).
Segarini et al., "The High Molecular Weight Receptor to Transforming Growth Factor–Beta Contains Glycosaminoglycan Chains" *J. Biol. Chem.* 263:8366–8370 (1988).
Cheifetz et al., "Heterodimeric Transforming Growth Factor Beta" *J. Biol. Chem.* 263:10783–10789 (1988a).
Cheifetz et al., "The Transforming Growth Factor–Beta Receptor Type III is a Membrane Proteoglycan" *J. Biol. Chem.* 263:16984–16991 (1988b).

(List continued on next page.)

*Primary Examiner*—David L. Fitzgerald
*Attorney, Agent, or Firm*—Campbell & Flores LLP

[57] ABSTRACT

The present invention provides a method of inhibiting an activity of a cell regulatory factor which includes contacting the cell regulatory factor with a purified polypeptide, the polypeptide including the cell regulatory factor binding domain of a protein which is characterized by a leucine-rich repeat of about 24 amino acids. The present invention relates to the ability of decorin, a 40,000 dalton protein that usually carries a glycosaminoglycan chain, to bind TGF-β. The invention also provides a novel cell regulatory factor designated MRF. Also provided are methods of identifying, detecting and purifying cell regulatory factors and proteins which bind and affect the activity of cell regulatory factors. The present invention further relates to methods for the prevention or reduction of scarring by administering decorin or a functional equivalent of decorin to a wound. The methods are particularly useful for dermal wounds resulting from burns, injuries or surgery. In addition, the present invention includes pharmaceutical compositions containing decorin or its functional equivalent and a pharmaceutically acceptable carrier useful in such methods. Finally, methods for preventing or inhibiting pathological conditions by administering decorin are also provided.

2 Claims, 20 Drawing Sheets

OTHER PUBLICATIONS

Fisher et al., "Deduced Protein Sequence of Bone Small Proteoglycan I (Biglycan) shows Homology with Proteoglycan II (Decorin) and Several Nonconnective Tissue Proteins in a Variety of Species" *J. Biol. Chem.* 264:4571–4576 (1989).

Andres et al., "Membrane–anchored and Soluble Forms of Betaglycan, a Polymorphic Proteoglycan that Binds Transforming Growth Factor–Beta" *J. Cell. Biol.* 109:3137–3145 (1989).

Kanzaki et al., "TGF–Beta 1 Binding Protein: A Component of the Large Latent Complex of TGF–Beta 1 with Muliple Repeat Sequences" *Cell* 61:1051–1061 (1990).

Brennan et al., "Effect of a Proteoglycan Produced by Rat Tumor Cells on Their Adhesion to Fibronectin–Collagen Substrata 1" *Cancer Res.* 43:4302–4307 (1983).

Brennan et al., "Chondroitin/Dermatan Sulfate Proteoglycan in Human Fetal Membranes" *J. of Biol. Chem.* 259:13742–13750 (1984).

Kresse et al., "Glycosaminoglycan–free Small Proteoglycan Core Protein Secreted by Fibroblasts from a Patient with a Syndrome Resembling Progeroid" *Am. J. Hum. Genet.* 41, (1987).

Yamaguchi et al., "Expression of Human Proteoglycan in Chinese Hamster Ovary Cells Inhibits Cell Proliferation" *Nature* 336:244–246 (1988).

Yamaguchi et al., "Negative Regulation of Transforming Growth Factor–Beta by the Proteoglycan Decorin" *Nature* 346:281–284 (1990).

Pearson et al., "The NH2–Terminal Amino Acid Sequence of Bovine Skin Proteodermatan Sulfate" *The Journal of Biol. Chem.* 258:15101–15104 (1983).

Ruoslahti, "Structure and Biology of Proteoglycans" *Ann. Rev. Cell Biol.* 4:229–255 (1988).

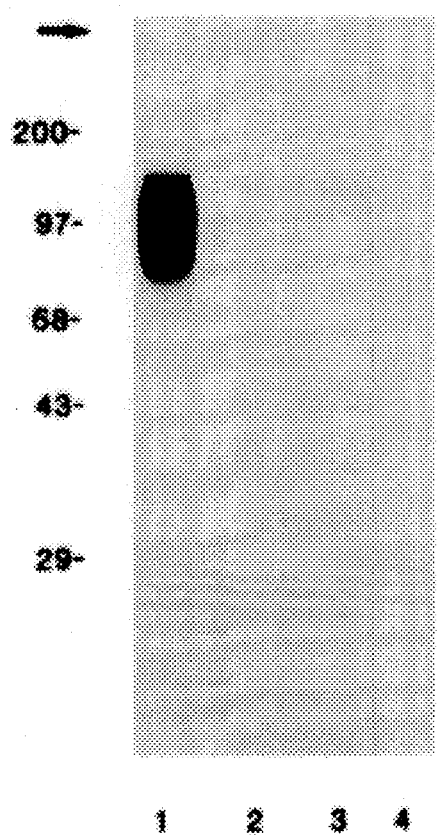 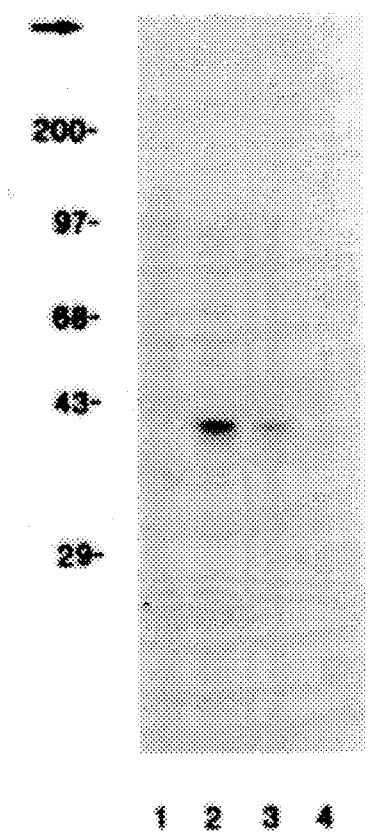

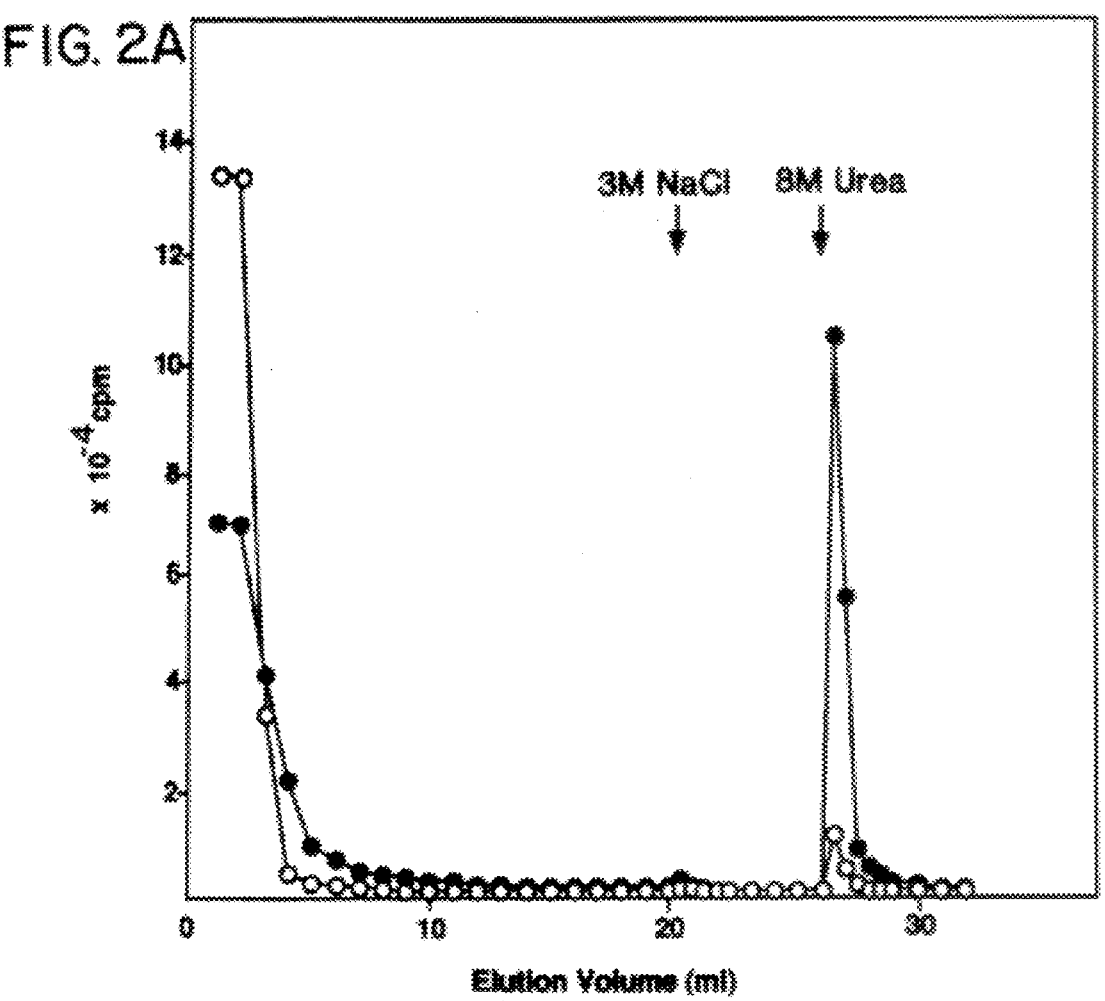
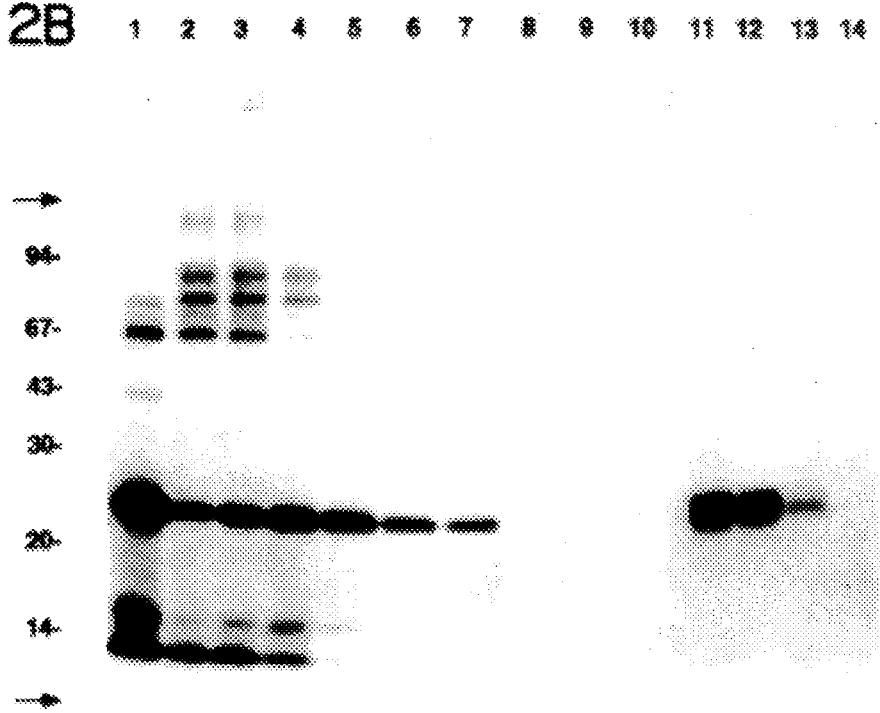

FIG. 6A
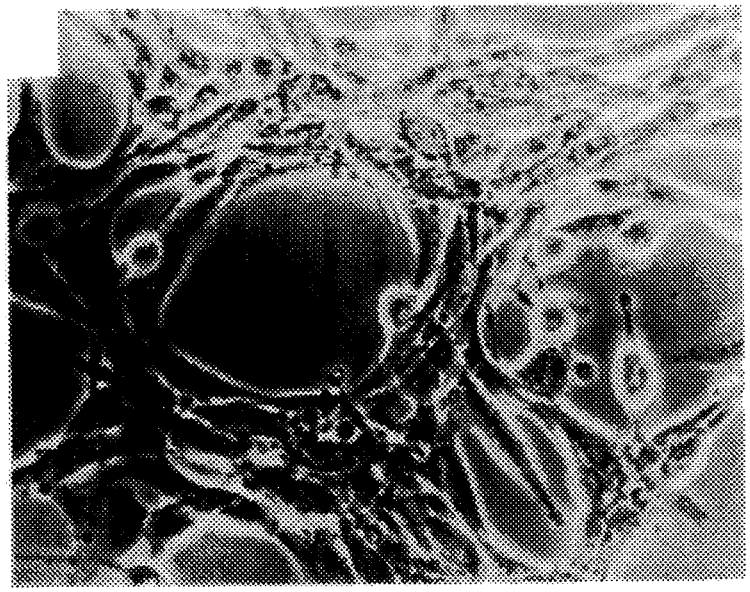
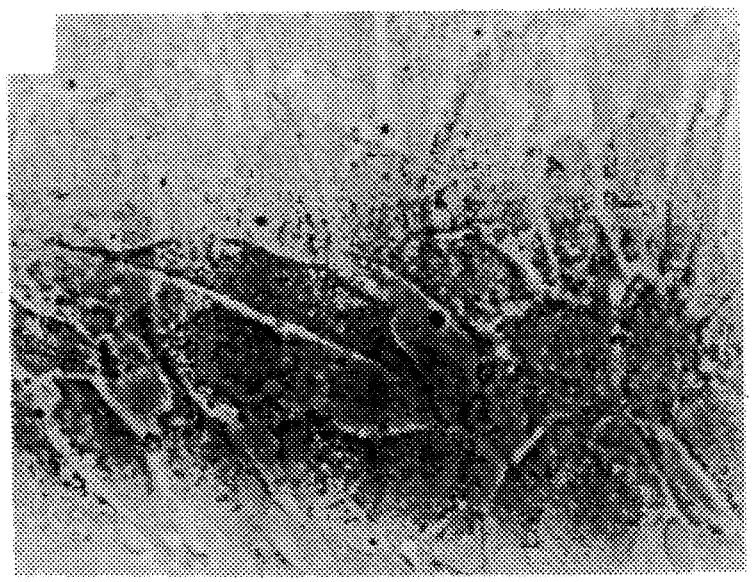
FIG. 6B

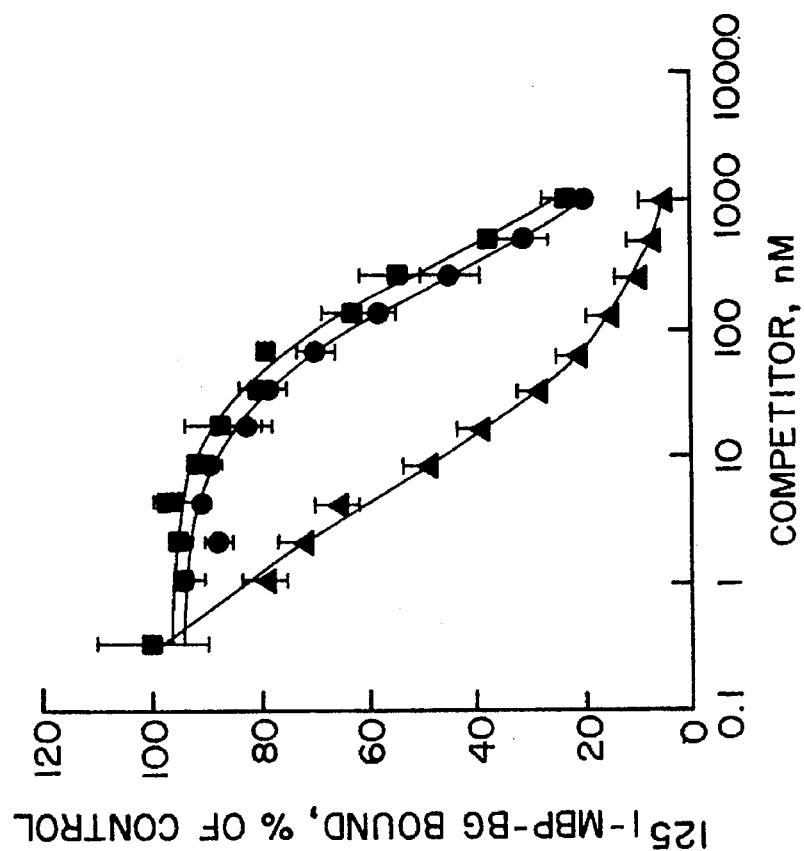
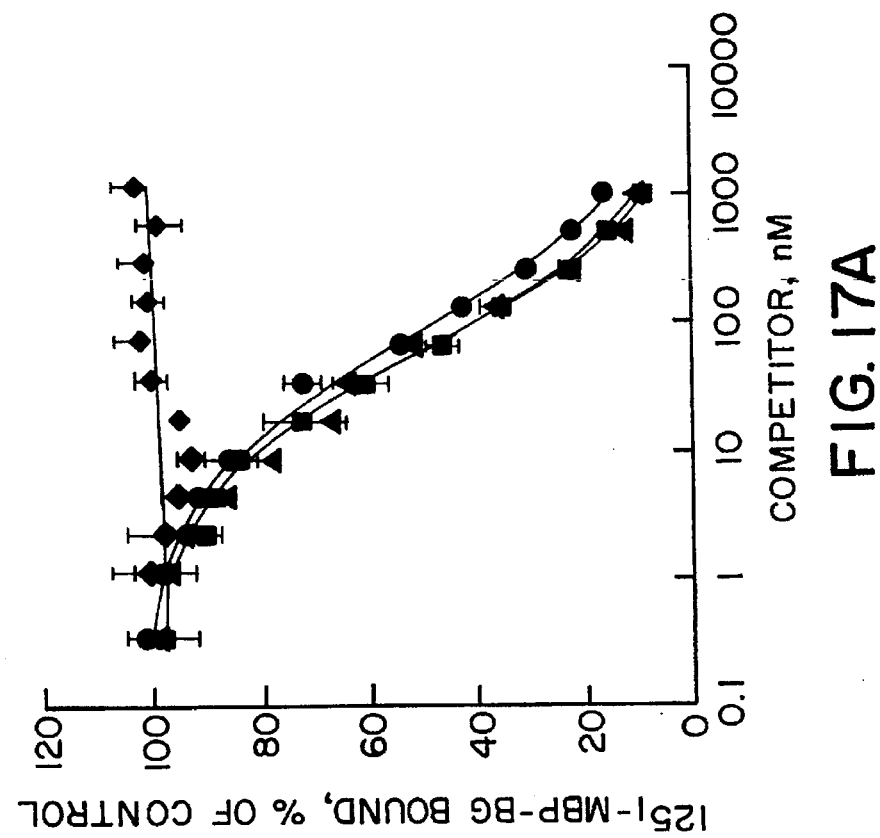

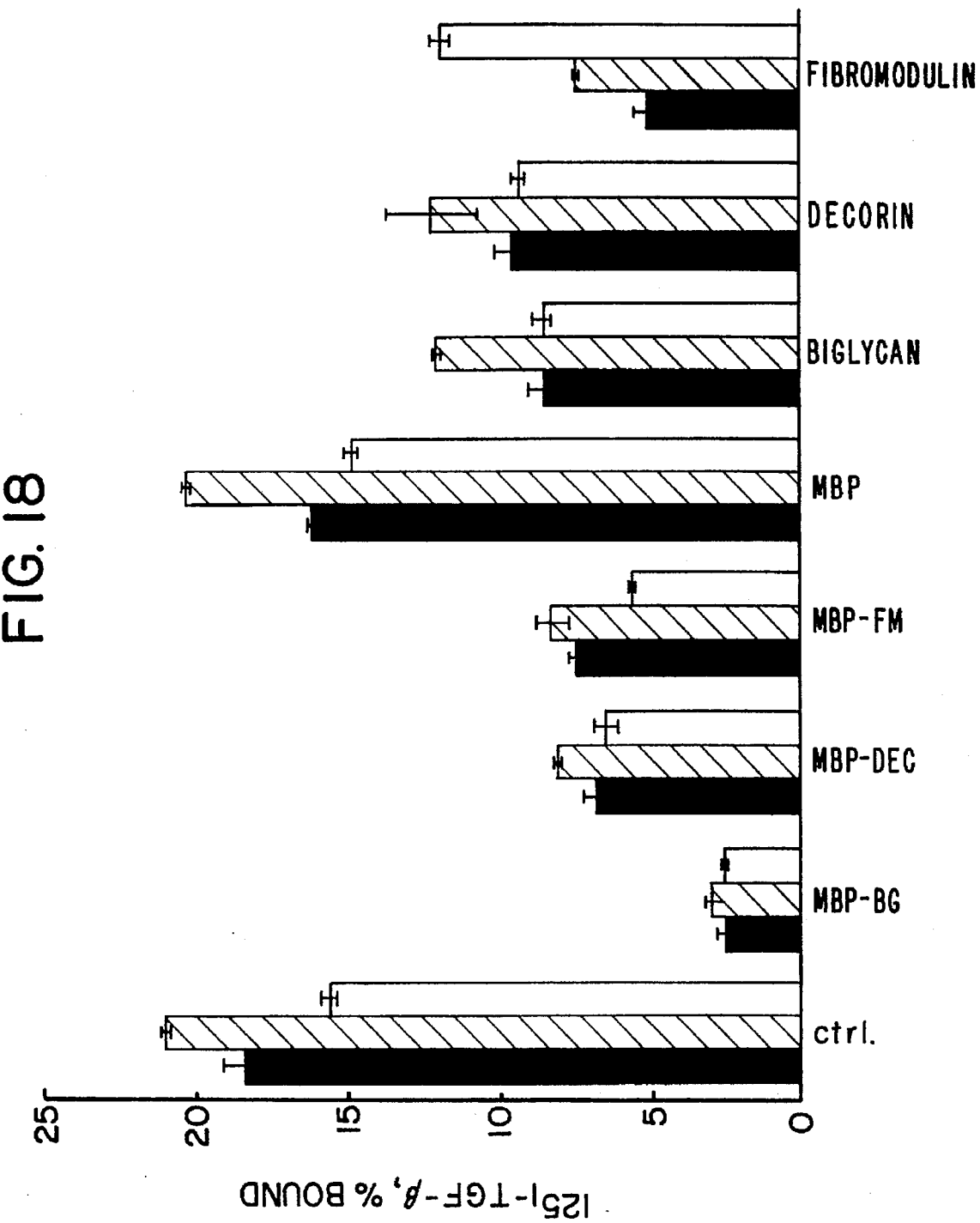

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Gln Trp Ala Ser Leu Leu Leu Leu Ala Gly Leu Phe Ser Leu Ser
 1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Leu Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
        115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asp Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Val Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile
    370                 375
```

( 2 ) INFORMATION FOR SEQ ID NO:2:

( i ) SEQUENCE CHARACTERISTICS:
        ( A ) LENGTH: 375 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Met | Gln | Trp | Ala | Ser | Ile | Leu | Leu | Leu | Ala | Gly | Leu | Cys | Ser | Leu | Ser |
|---|---|---|---|---|---|---|---|---|---|---|---|---|---|---|---|
| 1 | | | | 5 | | | | | 10 | | | | | 15 | |

| Trp | Ala | Gln | Tyr | Glu | Glu | Asp | Ser | His | Trp | Trp | Phe | Gln | Phe | Leu | Arg |
|---|---|---|---|---|---|---|---|---|---|---|---|---|---|---|---|
| | | | | 20 | | | | 25 | | | | | 30 | | |

| Asn | Gln | Gln | Ser | Thr | Tyr | Asp | Asp | Pro | Tyr | Asp | Pro | Tyr | Pro | Tyr | Glu |
|---|---|---|---|---|---|---|---|---|---|---|---|---|---|---|---|
| | | | 35 | | | | 40 | | | | | 45 | | | |

| Pro | Tyr | Glu | Pro | Tyr | Pro | Thr | Gly | Glu | Glu | Gly | Pro | Ala | Tyr | Ala | Tyr |
|---|---|---|---|---|---|---|---|---|---|---|---|---|---|---|---|
| | 50 | | | | | 55 | | | | | 60 | | | | |

| Gly | Ser | Pro | Pro | Gln | Pro | Glu | Pro | Arg | Asp | Cys | Pro | Gln | Glu | Cys | Asp |
|---|---|---|---|---|---|---|---|---|---|---|---|---|---|---|---|
| 65 | | | | | 70 | | | | | 75 | | | | | 80 |

| Cys | Pro | Pro | Asn | Phe | Pro | Thr | Ala | Met | Tyr | Cys | Asp | Asn | Arg | Asn | Leu |
|---|---|---|---|---|---|---|---|---|---|---|---|---|---|---|---|
| | | | | 85 | | | | | 90 | | | | | 95 | |

| Lys | Tyr | Leu | Pro | Phe | Val | Pro | Ser | Arg | Met | Lys | Tyr | Val | Tyr | Phe | Gln |
|---|---|---|---|---|---|---|---|---|---|---|---|---|---|---|---|
| | | | 100 | | | | | 105 | | | | 110 | | | |

| Asn | Asn | Gln | Ile | Ser | Ser | Ile | Gln | Glu | Gly | Val | Phe | Asp | Asn | Ala | Thr |
|---|---|---|---|---|---|---|---|---|---|---|---|---|---|---|---|
| | | | 115 | | | | | 120 | | | | | 125 | | |

| Gly | Leu | Leu | Trp | Ile | Ala | Leu | His | Gly | Asn | Gln | Ile | Thr | Ser | Asp | Lys |
|---|---|---|---|---|---|---|---|---|---|---|---|---|---|---|---|
| | 130 | | | | | 135 | | | | | 140 | | | | |

| Val | Gly | Lys | Lys | Val | Phe | Ser | Lys | Leu | Arg | His | Leu | Glu | Arg | Leu | Tyr |
|---|---|---|---|---|---|---|---|---|---|---|---|---|---|---|---|
| 145 | | | | | 150 | | | | | 155 | | | | | 160 |

| Leu | Asp | His | Asn | Asn | Leu | Thr | Arg | Ile | Pro | Ser | Pro | Leu | Pro | Arg | Ser |
|---|---|---|---|---|---|---|---|---|---|---|---|---|---|---|---|
| | | | | 165 | | | | | 170 | | | | | 175 | |

| Leu | Arg | Glu | Leu | His | Leu | Asp | His | Asn | Gln | Ile | Ser | Arg | Val | Pro | Asn |
|---|---|---|---|---|---|---|---|---|---|---|---|---|---|---|---|
| | | | 180 | | | | | 185 | | | | | 190 | | |

| Asn | Ala | Leu | Glu | Gly | Leu | Glu | Asn | Leu | Thr | Ala | Leu | Tyr | Leu | His | His |
|---|---|---|---|---|---|---|---|---|---|---|---|---|---|---|---|
| | | 195 | | | | | 200 | | | | | 205 | | | |

| Asn | Glu | Ile | Gln | Glu | Val | Gly | Ser | Ser | Met | Lys | Gly | Leu | Arg | Ser | Leu |
|---|---|---|---|---|---|---|---|---|---|---|---|---|---|---|---|
| | 210 | | | | | 215 | | | | | 220 | | | | |

| Ile | Leu | Leu | Asp | Leu | Ser | Tyr | Asn | His | Leu | Arg | Lys | Val | Pro | Asp | Gly |
|---|---|---|---|---|---|---|---|---|---|---|---|---|---|---|---|
| 225 | | | | | 230 | | | | | 235 | | | | | 240 |

| Leu | Pro | Ser | Ala | Leu | Glu | Gln | Leu | Tyr | Leu | Glu | His | Asn | Asn | Val | Phe |
|---|---|---|---|---|---|---|---|---|---|---|---|---|---|---|---|
| | | | | 245 | | | | | 250 | | | | | 255 | |

| Ser | Val | Pro | Asp | Ser | Tyr | Phe | Arg | Gly | Ser | Pro | Lys | Leu | Leu | Tyr | Val |
|---|---|---|---|---|---|---|---|---|---|---|---|---|---|---|---|
| | | | 260 | | | | | 265 | | | | | 270 | | |

| Arg | Leu | Ser | His | Asn | Ser | Leu | Thr | Asn | Asn | Gly | Leu | Ala | Ser | Asn | Thr |
|---|---|---|---|---|---|---|---|---|---|---|---|---|---|---|---|
| | | 275 | | | | | 280 | | | | | 285 | | | |

| Phe | Asn | Ser | Ser | Ser | Leu | Leu | Glu | Leu | Asp | Leu | Ser | Tyr | Asn | Gln | Leu |
|---|---|---|---|---|---|---|---|---|---|---|---|---|---|---|---|
| | 290 | | | | | 295 | | | | | 300 | | | | |

| Gln | Lys | Ile | Pro | Pro | Val | Ser | Thr | Asn | Leu | Glu | Asn | Leu | Tyr | Leu | Gln |
|---|---|---|---|---|---|---|---|---|---|---|---|---|---|---|---|
| 305 | | | | | 310 | | | | | 315 | | | | | 320 |

| Gly | Asn | Arg | Ile | Asn | Glu | Phe | Ser | Ile | Ser | Ser | Phe | Cys | Thr | Val | Val |
|---|---|---|---|---|---|---|---|---|---|---|---|---|---|---|---|
| | | | | 325 | | | | | 330 | | | | | 335 | |

| Asp | Val | Met | Asn | Phe | Ser | Lys | Leu | Gln | Val | Gln | Arg | Leu | Asp | Gly | Asn |
|---|---|---|---|---|---|---|---|---|---|---|---|---|---|---|---|
| | | | 340 | | | | | 345 | | | | | 350 | | |

| Glu | Ile | Lys | Arg | Ser | Ala | Met | Pro | Ala | Asp | Ala | Pro | Leu | Cys | Leu | Arg |
|---|---|---|---|---|---|---|---|---|---|---|---|---|---|---|---|
| | | 355 | | | | | 360 | | | | | 365 | | | |

| Leu | Ala | Ser | Leu | Ile | Glu | Ile |
|---|---|---|---|---|---|---|
| | 370 | | | | | 375 |

( 2 ) INFORMATION FOR SEQ ID NO:3:

( i ) SEQUENCE CHARACTERISTICS:
  ( A ) LENGTH: 368 amino acids
  ( B ) TYPE: amino acid
  ( D ) TOPOLOGY: linear ( i i ) MOLECULE TYPE: protein ( x i ) SEQUENCE DESCRIPTION: SEQ ID NO:3:

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Asn Val Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Asn
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

(2) INFORMATION FOR SEQ ID NO:4:

(i) SEQUENCE CHARACTERISTICS:
      (A) LENGTH: 359 amino acids
      (B) TYPE: amino acid
      (D) TOPOLOGY: linear (ii) MOLECULE TYPE: protein (xi) SEQUENCE DESCRIPTION: SEQ ID NO:4:

```
Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
    130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
            195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
            275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
            355
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..24

(xi) SEQUENCE DESCRIPTION: SEQ ID NO:5:

```
ATC GAG GGA AGG ATT TCA GAA TTC                              24
Ile Glu Gly Arg Ile Ser Glu Phe
 1               5
```

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:6:

```
Ile Glu Gly Arg Ile Ser Glu Phe
 1               5
```

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..12

(xi) SEQUENCE DESCRIPTION: SEQ ID NO:7:

```
ATG AGA GGA TCG                                              12
Met Arg Gly Ser
 1
```

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:8:

```
Met Arg Gly Ser
 1
```

USE OF FIBROMODULIN TO PREVENT OR REDUCE DERMAL SCARRING

This application is a continuation of application Ser. No. 07/978,931, filed Nov. 17, 1992, now abandoned, which is a continuation-in-part of U.S. Ser. No. 07/882,345, filed May 13, 1992, now abandoned, which is a continuation of U.S. Ser. No. 07/792,192, filed Nov. 14, 1991, now abandoned, which is a continuation-in-part of U.S. Ser. No. 07/467,888, filed Jan. 22, 1990, now abandoned, which is a continuation-in-part of U.S. Ser. No. 07/212,702, filed Jun. 28, 1988, now abandoned.

This invention was made with support of government grants CA 30199, CA 42507 and CA 28896 from the National Cancer Institute. Therefore, the United States government may have rights in the invention.

BACKGROUND OF THE INVENTION

This invention relates to cell biology and more specifically to the control of cell proliferation. Proteoglycans are proteins that carry one or more glycosaminoglycan chains. The known proteoglycans carry out a wide variety of functions and are found in a variety of cellular locations. Many proteoglycans are components of extracellular matrix, where they participate in the assembly of cells and effect the attachment of cells to the matrix.

One of the key functions of the extracellular matrix is the storage and presentation of growth factors to cells. Proteoglycans are important mediators of growth factor binding, and they have been shown to modulate the biological activities of a variety of growth factors through interaction via their glycosaminoglycan moieties as well as their core proteins (Ruoslahti, 1989; Ruoslahti and Yamaguchi, 1991).

Growth factors that bind to glycosaminoglycans include acidic and basic FGF (see Burgess and Maciag, 1989), GM-CSP, interleukin-3 (Roberts et al., 1988), pleiotrophin (Li et al., 1990), amphiregulin (Shoyab et al., 1988), HB-EGF (Higashiyama et al., 1991) and platelet factor 4 (Huang et al., 1982), each of which binds avidly to heparin and heparan sulfate. The binding of FGFs to heparin or to heparan sulfate proteoglycans protects the growth factors from proteolytic degradation and is thought to create a matrix-bound growth factor reservoir (Saksela et al., 1988; Gospodarowicz et al., 1990) from which the growth factor can be released in an active form by partial proteolysis of the proteoglycan core protein or through degradation of the heparan sulfate moiety of the proteoglycans (Saksela and Rifkin, 1990; Ishai-Michaeli et al., 1990). Basic FGF has to be bound to glycosaminoglycan to be able to interact with its signal transduction receptor (Yayon et al., 1991; Rapraeger et al., 1991).

The binding of TGF-β to proteoglycans represents a different type of growth factor-proteoglycan interaction. TGF-β has been demonstrated to bind to the core proteins of at least two proteoglycans. One of these proteoglycans is is decorin, a small interstitial extracellular matrix proteoglycan that can interact with TGF-β via its core protein (Yamaguchi et al., 1990). Decorin, also known as PG-II or PG-40, is a small proteoglycan produced by fibroblasts. Its core protein has a molecular weight of about 40,000 daltons. The core has been sequenced (Krusius and Ruoslahti, Proc. Natl. Acad. Sci. USA 83: 7683 (1986); Day et al. Blochem. J. 248: 801 (1987), both of which are incorporated herein by reference) and it is known to carry a single glycosaminoglycan chain of a chondroitin sulfate/dermatan sulfate type (Pearson, et al., J. Biol. Chem. 258: 15101 (1983), which is incorporated herein by reference). The only previously known function for decorin is binding to type I and type II collagen and its effect on the fibril formation by these collagens (Vogel, et al., Biochem. J. 223: 587 (1984); Schmidt et al., J. Cell Biol. 104: 1683, (1987)). Decorin (Krusius and Ruoslahti, 1986) is the prototype of a group of proteoglycans characterized by core proteins of ~40 kDa that consist mainly of leucine-rich repeats of 20 to 24 amino acids (Patthy, 1987). So far, four members of this group of proteoglycans have been cloned; in addition to decorin, these are biglycan (Fisher et al., 1989), fibromodulin (Oldberg et al., 1989) and lumican (Blochberger et al., 1992). Decorin and biglycan are ubiquitous, although they show a quite divergent localization within tissues, with decorin found more in the extracellular matrix of tissues where it is bound to type I collagen (Vogel et al., 1984; Scott, 1986; Brown and Vogel, 1989) and biglycan localized more closely around cells (Bianco et al., 1990). Fibromodulin has a somewhat more restricted distribution with high concentrations in cartilage, tendon and sclera, while low in skin and mineralized bone (Heinegard et al., 1986). Lumican is found mainly in the cornea (Blochberger et al., 1992). Together, these proteins form a superfamily of proteins (Ruoslahti, Ann. Rev. Cell Biol. 4: 229, (1988); McFarland et al., Science 245: 494 (1989)).

The second type of TGF-β-binding proteoglycan is the type III TGF-β receptor, betaglycan (Segarini and Seyedin et al., 1988; Andres et al., 1989). Betaglycan is a cell membrane proteoglycan (López-Casillas et al., 1991; Wang et al., 1991) that apparently is not involved in the TGF-β signal transduction pathway but may function as a cell-surface TGF-β reservoir presenting TGF-β to its signal transduction receptors.

Transforming growth factor βs (TGF-β) are a family of multi-functional cell regulatory factors produced in various forms by many types of cells (for review see Sporn et al., J. Cell Biol. 105: 1039, (1987)). Five different TGF-β's are known, but the functions of only two, TGF-β1 and TGF-β2, have been characterized in any detail. TGF-β's are the subject of U.S. Pat. Nos. 4,863,899; 4,816,561; and 4,742,003 which are incorporated by reference. TGF-β1 and TGF-β2 are publicly available through many commercial sources (e.g. R & D Systems, Inc., Minneapolis, Minn.). In some cells, TGF-β promotes cell proliferation, in others it suppresses proliferation. A marked effect of TGF-β is that it promotes the production of extracellular matrix proteins and their receptors by cells (for review see Keski-Oja et al., J. Cell Biochem 33: 95 (1987); Massague, Cell 49: 437 (1987); Roberts and Sporn in "Peptides Growth Factors and Their Receptors" [Springer-Verlag, Heidelberg] (1989)).

While TGF-β has many essential cell regulatory functions, improper TGF-β activity can be detrimental to an organism. Since the growth of mesenchyme and proliferation of mesenchymal cells is stimulated by TGF-β, some tumor cells may use TGF-β as an autocrine growth factor. Therefore, if the growth factor activity of TGF-β could be prevented, tumor growth could be controlled. In other cases the inhibition of cell proliferation by TGF-β may be detrimental, in that it may prevent healing of injured tissues. The stimulation of extracellular matrix production by TGF-β is important in situations such as wound healing. However, in some cases the body takes this response too far and an excessive accumulation of extracellular matrix ensues. An example of excessive accumulation of extracellular matrix is glomerulonephritis, a disease with a detrimental involvement of TGF-β.

Thus, there exists a critical need to develop compounds that can modulate the effects of cell regulatory factors such as TGF-β. The present invention satisfies this need and provides related advantages.

SUMMARY OF THE INVENTION

The present invention provides a method of inhibiting an activity of a cell regulatory factor comprising contacting the cell regulatory factor with a purified polypeptide, wherein the polypeptide comprises a cell regulatory factor binding domain of a protein and wherein the protein is characterized by a leucine-rich repeat of about 24 amino acids. In a specific embodiment, the present invention relates to the ability of decorin, a 40,000 dalton protein that usually carries a glycosaminoglycan chain, to bind TGF-B. The invention also provides a novel cell regulatory factor designated Morphology Restoring Factor, (MRF). Also provided are methods of identifying, detecting and purifying cell regulatory factors and proteins which bind and affect the activity of cell regulatory factors.

The present invention further relates to methods for the prevention or reduction of scarring by administering decorin or a functional equivalent of decorin to a wound. The methods are particularly useful for dermal wounds resulting from burns, injuries or surgery. In addition, the present invention includes pharmaceutical compositions containing decorin or its functional equivalent and a pharmaceutically acceptable carrier useful in such methods. Finally, methods for preventing or inhibiting pathological conditions by administering decorin are also provided.

BRIEF DESCRIPTION OF THE FIGURES

FIGS. 1A and 1B show expression of decorin cDNA containing a mutation of the serine acceptor site to alanine. COS-1 cultures were transfected with cDNA coding for wild-type decorin (lane 1), decorin in which the serine-4 residue was replaced by an alanine (lane 2), or decorin in which the serine-4 residue was replaced by a threonine (lane 3). Immunoprecipitations were performed with an anti-decorin antibody and medium which was labeled with $^{35}$S-sulfate (FIG. 1A) or $^3$H-leucine (FIG. 1B). Lane 4 shows an immunoprecipitate from mock transfected COS-1 cultures. Arrow indicates top of gel. The numbers indicate $M_r \times 10^{-3}$ for molecular weight standards.

FIGS. 2A–12B show binding of [$^{125}$I]-TGF-β1 to decorin-Sepharose. FIG. 2A shows fractionation of [$^{125}$I]-TGF-β1 by decorin-Sepharose affinity chromatography. [$^{125}$I]-TGF-β1 (5×10$^5$ cpm) was incubated in BSA-coated polypropylene tubes with 0.2 ml of packed decorin-Sepharose (●) or gelatin-Sepharose (○) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer. FIG. 2B shows the analysis of eluents of decorin-Sepharose affinity chromatography by SDS-polyacrylamide gel under nonreducing conditions. Lane 1: the original [$^{125}$I]-labeled TGF-β1 sample; lanes 2–7: flow through and wash fractions; lanes 8–10: 3M NaCl fractions; lanes 11–14: 8M urea fractions. Arrows indicate the top and bottom of the 12% separating gel.

FIG. 3A shows the competition of [$^{125}$I]-TGF-β1 binding to decorin-coated microtiter wells by recombinant decorin (●), decorin isolated from bovine skin (PGII) (■), biglycan isolated from bovine articular cartilage (PGI) (▲), chicken cartilage proteoglycan (○), and BSA (□). Each point represents the mean of duplicate determinants. FIG. 3B shows the competition of [$^{125}$I]-TGF-β1 binding with chondroitinase ABC-treated proteoglycans and BSA. The concentrations of competitors were expressed as intact proteoglycan. The symbols are the same as in FIG. 3A.

FIG. 4A shows inhibition of TGF-β1-induced proliferation of CHO cells by decorin. The [$^3$H]Thymidine incorporation assay was performed as described in the legend of FIG. 1 in the presence of 5 ng/ml of TGF-β1 and the indicated concentrations of purified decorin (●) or BSA (○). At the concentration used, TGF-β1 induced a 50% increase of [$^3$H]thymidine incorporation in the CHO cells. The data represent percent neutralization of this growth stimulation; i.e. [$^3$H]thymidine incorporation in the absence of either TGF-β1 or decorin=0%, incorporation in the presence of TGF-β but not decorin= 100%. Each point shows the mean±standard deviation of triplicate samples. FIG. 4B shows neutralization of TGF-β1-induced growth inhibition in MvLu cells by decorin. Assay was performed as in A except that TGF-β1 was added at 0.5 ng/ml. This concentration of TGF-β1 induces 50% reduction of [$^3$H]thymidine incorporation in the MvLu cells. The data represent neutralization of TGF-β-induced growth inhibition; i.e. [$^3$H]thymidine incorporation in the presence of neither TGF-β or decorin=100%; incorporation in the presence of TGF-β but not decorin=0%.

FIGS. 6A and 6B show micrographs demonstrating a decorin-binding cell regulatory activity that is not suppressed by antibodies to TGF-β1.

FIG. 7A shows the non-reduced lysate of HepG2 cells resolved on 4–12% SDS-PAGE. FIG. 7B shows the reduced lysate resolved on 4–12% SDS-PAGE. The reduction of intensity of β glycan band (approximately 300 kDa) and uncross-linked band (free TGF-β, 25 kDa) in the presence of decorin (10,000×molar excess) is shown.

FIG. 8A shows the resolution of the lysate on 4–12% SDS-PAGE under non-reduced conditions, while FIG. 8B shows the results under reduced conditions.

FIG. 9 shows that decorin (DC-9, DC-12) and biglycan inhibit the binding of [$^{125}$I]-TGF-β to immobilized decorin.

FIG. 10 shows the concentration dependence of decorin inhibition of [$^{125}$I]-TGF-β binding to HepG2 cells.

FIG. 11 shows the amino acid sequence of human fibromodulin deduced from cDNA. The human fibromodulin sequence (SEQ. ID. NO.1) is shown aligned with the amino acid sequences of bovine fibromodulin (Oldberg et al., 1989) (SEQ. ID. NO:2), human decorin (Krusius and Ruoslahti, 1986) (SEQ. ID. NO.4) and human biglycan (Fisher et al., 1989) (SEQ. ID. NO.3). A star marks the sequence position where the $NH_2$-termini of the proteoglycan core proteins lacking their predicted signal sequences were fused to $E.$ $coli$-maltose binding protein (MBP) with two additional amino acids, glycine and serine, added at the linkage site. Identical amino acids are boxed.

FIG. 12 shows the construction of prokaryotic expression vector for proteoglycan fusion proteins. The parent vector pQE-8 was modified by insertion of a BglII/BamHI-MBP fragment (SEQ. ID. NOS. 5 and 6). This fragment also included a factor Xa protease cleavage site and provided a unique BamHI cloning site for introduction of the proteoglycan core protein inserts. RBS=ribosomal binding site; 6xHis=coding sequence for consecutive six histidines; MBP=coding sequence for $E.$ $coli$-maltose binding protein; to=transcriptional terminator 'to' of phage lambda (Schwarz et al., 1987); cat=promotor-free gene for chloramphenicol acetyltransferase; T1=transcriptional terminator T1 of the $E.$ $coli$ rrnB operon (Brosius et al., 1981). The RBS and 6xHis region are separated by the peptide "Met Arg Gly Ser" (SEQ. ID. NOS. 7 and 8).

FIG. 17A and 17B show the inhibition of the binding of biglycan fusion protein to TGF-β1 by proteoglycan fusion proteins and intact proteoglycans. Binding of $^{125}$I-MBP-biglycan to TGF-β1 was measured in the presence of the indicated concentrations of (FIG. 17A) unlabeled MBP-BG (■), MBP-DEC (●), MBP-FM (▲) or MBP (♦) or (FIG. 17B) purified biglycan (■), decorin (●) or fibromodulin (▲). After incubation of 6 hours at 37° C., the wells were washed three times and counted in a gamma counter. Binding (±S.D.) is expressed as percent of radiolabel bound in the absence of competitor.

FIG. 18 shows the competition for the binding of radiolabeled TGF-β1, -β2 and -β3 to microtiter wells coated with biglycan fusion protein. The binding of $^{125}$I-labeled TGF-β1 (solid bars), TGF-β2 (hatched bars) or TGF-β3 (open bars) (50,000 cpm/well, specific activities 5,000 to 7,000 Cl/mmol) to surface-bound MBP-biglycan (coating concentration 10 μg/ml. 75 μl/well) was studied in the absence (control) or presence of unlabeled MBP-BG, MB-DEC, MBP-FM, MBP, biglycan, decorin or fibromodulin (1 μM). Binding was corrected for nonspecific binding as is expressed as percent (±S.D.) of the total amount of labeled TGF-β1, 2 or 3 that was added to the wells.

(FIG. 19A) Subconfluent cultures of MvLu mink lung cells cultured in 48-well plates were incubated with $^{125}$I-TGF-β1 (100 pM) in the presence (n.s.) or absence (B$_o$) of unlabeled TGF-β1 (20 nM) or the indicated concentrations of proteoglycan fusion proteins in a total volume of 100 μl. After incubation for 4 hours at 4° C., the cells were washed four times. The cells were then solubilized for 40 min in 1% Triton-X 100 and assayed for radioactivity in a gamma counter. Binding (±S.D., n=3) is expressed as percent of the total amount of $^{125}$I-TGF-β1 that was added. (FIG. 19B) Mink lung cells were incubated with $^{125}$I-TGF-β1 (100 pM) in the absence or presence of unlabeled TGF-β (20 nM) or MBP-fusion proteins (3 μM) in 24-well plates. After incubation for 4 hours at 4° C., the cells were treated with the cross-linker disuccinimidyl suberate and analyzed by $NaDodSO_4$-PAGE and autoradiography. Binding in the absence of competitor (a), with TGF-β1 (b), MBP-BG (c), MBP-DEC (d), MBP-FM (e) or MBP (f). The positions of pre-stained marker proteins are indicated. The positions of the TGF-β type I and type II receptors and of betaglycan (β-G) are indicated. Arrows point to the receptors and betaglycan (β-G).

DETAILED DESCRIPTION OF THE INVENTION

Figure 3A:
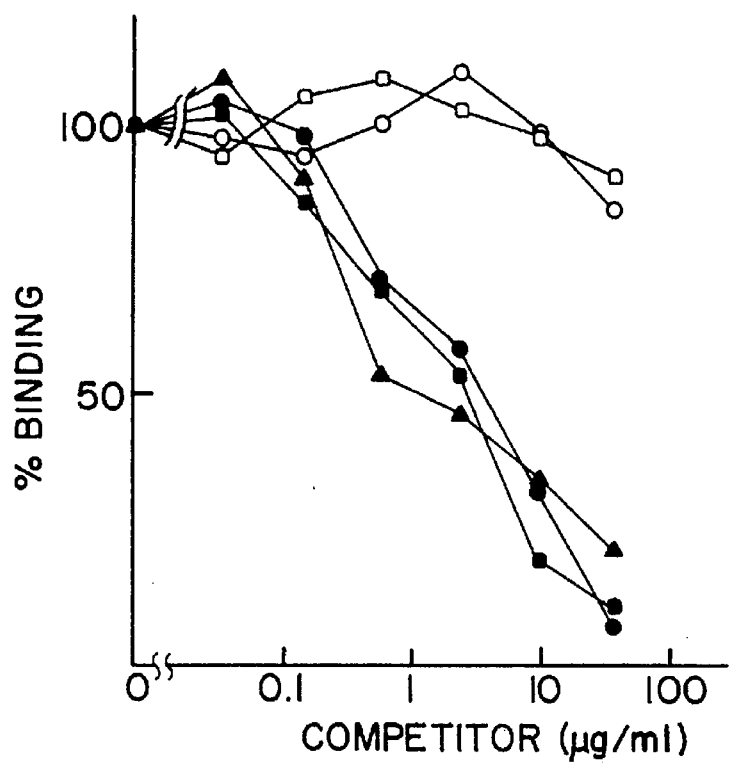
FIGS. 3A and 3B shows the inhibition of binding of [$^{125}$I]-TGF-β1 to decorin by proteoglycans and their core proteins.

Increased TGF-β production has been found to be an important element in a number of fibrotic diseases that are characterized by an accumulation of extracellular matrix components (Border and Ruoslahti, 1992). Besides fibronectin, collagens, and tenascin (Ignotz and Massague, 1986; Varga et al., 1987; Pearson et al., 1988), TGF-β also upregulates the expression of proteoglycans (Bassols and Massagure, 1988). In mesangial cells both decorin and biglycan can increase as much as 50-fold after induction by TGF-β (Border et al., 1990a), whereas in fibroblasts only biglycan seems to be elevated (Romaris et al., 1992; Kahari et al., 1991). Fibromodulin has not been studied in this regard. TGF-β plays a pivotal role in the pathogenesis of experimentally induced glomerulonephritis, the most critical manifestation of which is the accumulation of extracellular matrix in the glomeruli (Border et al., 1990). A recent study shows that injection of recombinant decorin into glomerulonephritic rats can suppress the matrix accumulation (Border et al., 1992). The present invention indicates that fibromodulin can be even more effective in that situation. The TGF-β neutralizing activities of the decorin-type proteoglycans indicates that new types of therapeutics can be developed based on these molecules.

The invention provides a method of inhibiting an activity of a cell regulatory factor comprising contacting the cell regulatory factor with a purified polypeptide, wherein the polypeptide comprises the cell regulatory factor binding domain of a protein and wherein the protein is characterized by a leucine-rich repeat of about 24 amino acids. Since diseases such as cancer result from uncontrolled cell proliferation, the invention can be used to treat such diseases.

By "cell regulatory factor" is meant a molecule which can regulate an activity of a cell. The cell regulatory factors are generally proteins which bind cell surface receptors and include growth factors. Examples of cell regulatory factors include the five TGF-β's, platelet-derived growth factor, epidermal growth factor, insulin like growth factor I and II, fibroblast growth factor, interleukin-2, nerve growth factor, hemopoietic cell growth factors (IL-3, GM-CSF, M-CSF, G-CSF, erythropoietin) and the newly discovered Morphology Restoring Factor, hereinafter "MRF". Different regulatory factors can be bound by different proteins which can affect the regulatory factor's activity. For example, TGF-β1 is bound by decorin, biglycan and fibromodulin, and MRF is bound by decorin.

By "cell regulatory factor binding domain" is meant the fragment of a protein which binds to the cell regulatory factor. While the specific examples set forth herein utilize proteins, it is understood that a protein fragment which retains the binding activity is included within the scope of the invention. Fragments which retain such activity can be recognized by their ability to competitively inhibit the binding of, for example, decorin to TGF-β, or of other polypeptides containing leucine-rich repeats to their cognate growth factors. As an example, fragments can be obtained by digestion of the native polypeptide or by synthesis of fragments based on the known amino acid sequence. Such fragments can then be used in a competitive assay to determine whether they retain binding activity. For example, decorin can be attached to an affinity matrix, as by the method of Example II. Labelled TGF-β, and the fragment in question can then be contacted with the affinity matrix and the amount of TGF-β bound thereto determined.

As used herein, "decorin" refers to a proteoglycan having substantially the structural characteristics attributed to it in Krusius and Ruoslahti, supra. Human fibroblast decorin has substantially the amino acid sequence presented in Krusius and Ruoslahti, supra. "Decorin" refers both to the native composition and to modifications thereof which substantially retain the functional characteristics. Decorin core protein refers to decorin that no longer is substantially substituted with glycosaminoglycan and is included in the definition of decorin. Decorin can be rendered glycosaminoglycan-free by mutation or other means, such as by producing recombinant decorin in cells incapable of attaching glycosaminoglycan chains to a core protein.

Functional equivalents of decorin include modifications of decorin that retain its functional characteristics and molecules that are homologous to decorin, such as biglycan and fibromodulin, for example, that have the similar functional activity of decorin. Modifications can include, for example, the addition of one or more side chains that do not interfere with the functional activity of the decorin core protein.

Since the regulatory factor binding proteins each contain leucine-rich repeats of about 24 amino acids which can constitute 80% of the protein, it is likely that the fragments which retain the binding activity occur in the leucine-rich repeats. However, it is possible the binding activity resides in the carboxy-terminal amino acids or the junction of the repeats and the carboxy terminal amino acids.

The invention teaches a general method whereby one skilled in the art can identify proteins which can bind to cell regulatory factors or identify cell regulatory factors which bind to a certain family of proteins. The invention also teaches a general method whereby these novel proteins or known existing proteins can be assayed to determine if they affect an activity of a cell regulatory factor. Specifically, the invention teaches the discovery that decorin and biglycan bind TGF-βs and MRF and that such binding can inhibit the cell regulatory functions of TGF-ββs. Further, both decorin and biglycan are about 80% homologous and contain a leucine-rich repeat of about 24 amino acids in which the arrangement of the leucine residues is conserved. As defined each repeat generally contains at least two leucine residues and can contain five or more. These proteoglycans are thus considered members of the same protein family. See Ruoslahti, supra, Fisher et al., J. Biol. Chem., 264: 4571–4576 (1989) and Patthy, J. Mol. Biol., 198: 567–577 (1987), all of which are incorporated by reference. Other known or later discovered proteins having this leucine-rich repeat, i.e., fibromodulin, would be expected to have a similar cell regulatory activity. The ability of such proteins to bind cell regulatory factors could easily be tested, for example by affinity chromatography or microtiter assay as set forth in Example II, using known cell regulatory factors, such as TGF-βs. Alternatively, any later discovered cell regulatory factor could be tested, for example by affinity chromatography using one or more regulatory factor binding proteins. Once it is determined that such binding occurs, the effect of the binding on the activity of all regulatory factors can be determined by methods such as growth assays as set forth in Example III. Moreover, one skilled in the art could simply substitute a novel cell regulatory factor for a TGF-β or a novel leucine-rich repeat protein for decorin or biglycan in the Examples to determine their activities. Thus, the invention provides general methods to identify and test novel cell regulatory factors and proteins which affect the activity of these factors.

The invention also provides a novel purified compound comprising a cell regulatory factor attached to a purified polypeptide wherein the polypeptide comprises the cell regulatory factor binding domain of a protein and the protein is characterized by a leucine-rich repeat of about 24 amino acids.

The invention further provides a novel purified protein, designated MRF, having a molecular weight of about 20 kd, which can be isolated from CHO cells, copurifies with decorin under nondissociating conditions, separates from decorin under dissociating conditions, changes the morphology of transformed 3T3 cells, and has an activity which is not inhibited with anti-TGF-β1 antibody. Additionally, MRF separates from TGF-β1 in HPLC.

The invention still further provides a method of purifying a cell regulatory factor comprising contacting the regulatory factor with a protein which binds the cell regulatory factor and has a leucine-rich repeat of about 24 amino acids and to purify the regulatory factor which becomes bound to the protein. The method can be used, for example, to purify TGF-β1 by using decorin.

The invention additionally provides a method of treating a pathology caused by a TGF-β-regulated activity comprising contacting the TGF-β with a purified polypeptide, wherein the polypeptide comprises the TGF-β binding domain of a protein and wherein the protein is characterized by a leucine-rich repeat of about 24 amino acids, whereby the pathology-causing activity is prevented or reduced. While the method is generally applicable, specific examples of pathologies which can be treated include cancer, a fibrotic disease, and glomerulonephritis. In fibrotic cancer, for example, decorin can be used to bind TGF-β, destroying TGF-β's growth stimulating activity on the cancer cell. Other proliferative pathologies include rheumatoid arthritis, arteriosclerosis, adult respiratory distress syndrome, cirrhosis of the liver, fibrosis of the lungs, post-myocardial infarction, cardiac fibrosis, post-angioplasty restenosis, renal interstitial fibrosis and certain dermal fibrotic conditions such as keloids and scarring.

The present invention also provides a method of preventing the inhibition of a cell regulatory factor. The method comprises contacting a protein which inhibits an activity of a cell regulator factor with a molecule which inhibits the activity of the protein. For example, decorin could be bound by a molecule, such as an antibody, which prevents decorin from binding TGF-βs, thus preventing decorin from inhibiting the TGF-βs' activity. Thus, the TGF-βs wound healing activity could be promoted by binding TGF-β1 inhibitors.

Figure 10:
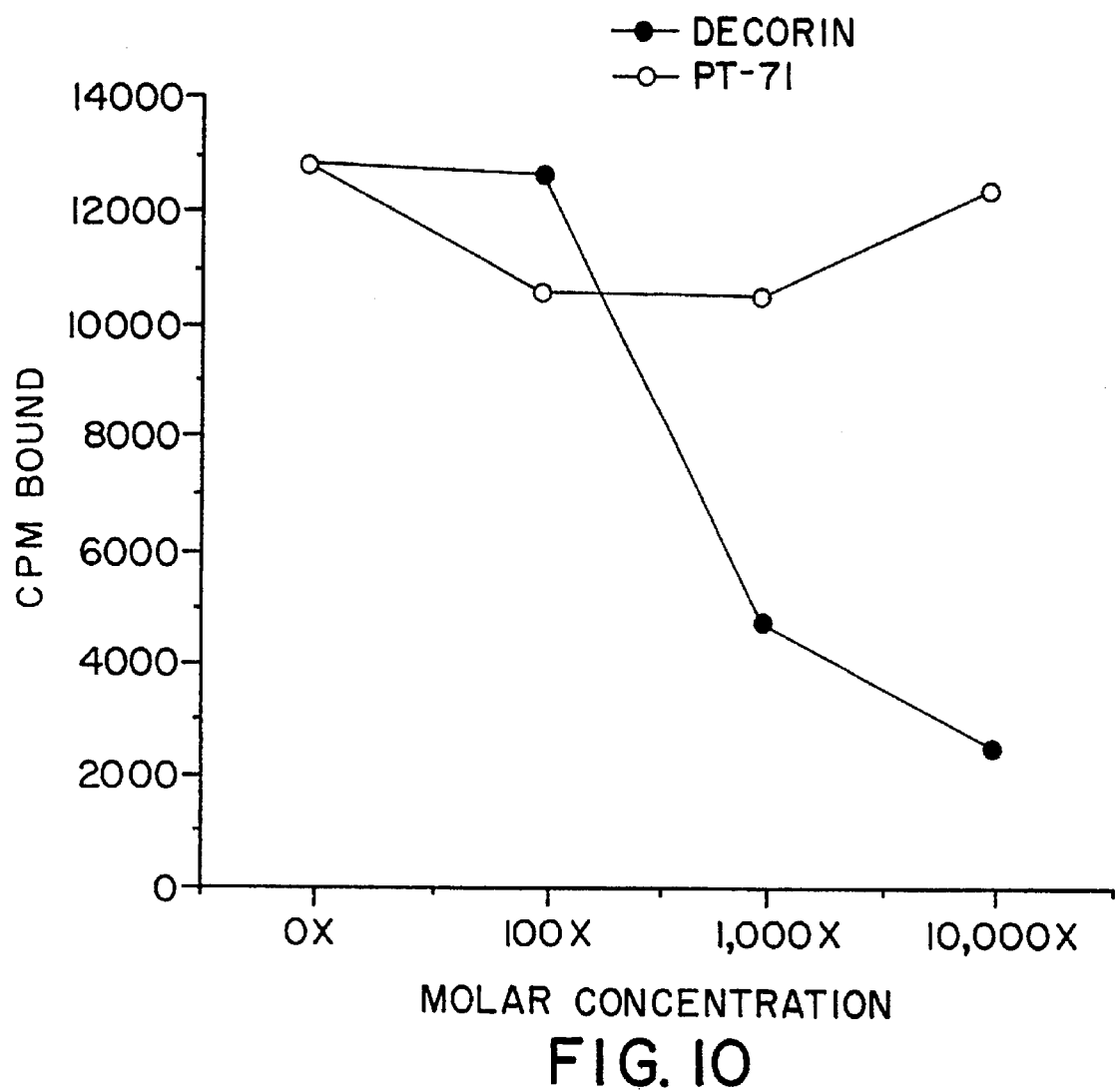

In addition, decorin has been found to inhibit the binding of TGF-βs to their receptors. FIGS. 7, 8 and 10 show the results of these studies in which cells bearing TGF-β receptors (betaglycan) were incubated with TGF-β in the presence and absence of decorin.

The present invention further relates to methods for the prevention or reduction of scarring by administering decorin or a functional equivalent of decorin to a wound. Dermal scarring is a process, following a variety of dermal injuries, that results in the excessive accumulation of fibrous tissue comprising collagen, fibronectin, and proteoglycans. The induction of fibrous matrix accumulation is a result of growth factor release at the wound site by platelets and inflammatory cells. The principal growth factor believed to induce the deposition of fibrous scar tissue is transforming growth factor-β (TGF-β). Decorin binds and neutralizes a variety of biological functions of TGF-β, including the induction of extracellular matrix. Due to the lack of elastic property of this fibrous extracellular matrix, the scar tissue resulting from a severe dermal injury often impairs essential tissue function and can result in an unsightly scar.

The advantage of using decorin or a functional equivalent, such as biglycan or fibromodulin, in the methods of the present invention is that it is a normal human protein and is believed to be involved in the natural TGF-B regulatory pathway. Thus, decorin can be used to prevent or reduce dermal scarring resulting from burn injuries, other invasive skin injuries, and cosmetic or reconstructive surgery.

Decorin-treated wounds have been found to exhibit essentially no detectable scarring compared to control wounds not treated with decorin. The TGF-β-induced scarring process has been shown to be unique to adults and third trimester human fetuses, but is essentially absent in fetuses during the first two trimesters. The absence of scarring in fetal wounds has been correlated with the absence of TGF-β in the wound bed. In contrast, the wound bed of adult tissue is heavily deposited with TGF-β and the fully healed wound is replaced by a reddened, furrowed scar containing extensively fibrous, collagenous matrix. The decorin-treated wounds were histologically normal and resembled fetal wounds in the first two trimesters.

In addition, the present invention further relates to a pharmaceutical composition containing decorin or its functional equivalent, such as biglycan or fibromodulin, and a pharmaceutically acceptable carrier useful in the above methods. Pharmaceutically acceptable carriers include, for example, hyaluronic acid, and aqueous solutions such as bicarbonate buffers, phosphate buffers, Ringer's solution and physiological saline supplemented with 5% dextrose or human serum albumin, if desired. The pharmaceutical compositions can also include other agents that promote wound healing known to those skilled in the art. Such agents can include, for example, biologically active chemicals and polypeptides, including RGD-containing polypeptides attached to a biodegradable polymer as described in PCT WO 90/06767, published on Jun. 28, 1990, and incorporated herein by reference. Such polypeptides can be attached to polymers by any means known in the art, including covalent or ionic binding, for example.

It is understood that modifications which do not substantially affect the activity of the various molecules of this invention including TGF-β, MRF, decorin, biglycan and fibromodulin are also included within the definition of those molecules. It is also understood that the core proteins of decorin, biglycan and fibromodulin are also included within the definition of those molecules.

The following examples are intended to illustrate but not limit the invention.

EXAMPLE I

EXPRESSION AND PURIFICATION OF RECOMBINANT DECORIN AND DECORIN CORE PROTEIN

Expression System

The 1.8 kb full-length decorin cDNA described in Krusius and Ruoslahti, Proc. Natl. Acad. Sci. USA 83: 7683 (1986), which is incorporated herein by reference, was used for the construction of decorin expression vectors. For the expression of decorin core protein, cDNA was mutagenized so the fourth codon, TCT, coding for serine, was changed to ACT coding for threonine, or GCT coding for alanine. This was engineered by site-directed mutagenesis according to the method of Kunkel, Proc. Natl. Acad. Sci USA 82: 488 (1985), which is incorporated herein by reference. The presence of the appropriate mutation was verified by DNA sequencing.

The mammalian expression vectors pSV2-decorin and pSV2-decorin/CP-thr4 core protein were constructed by ligating the decorin cDNA or the mutagenized decorin cDNA into 3.4 kb HindIII-Bam HI fragment of pSV2 (Mulligan and Berg, Science 209: 1423 (1980), which is incorporated herein by reference).

Dihydrofolate reductase (dhfr)-negative CHO cells (CHO-DG44) were cotransfected with pSV2-decorin or pSV2-decorin/CP and pSV2dhfr by the calcium phosphate coprecipitation method. The CHO-DG44 cells transfected with pSV2-decorin are deposited with the American Type Culture Collection under Accession Number ATCC No. CRL 10332. The transfected cells were cultured in nucleoside-minus alpha-modified minimal essential medium (α-MEM), (GIBCO, Long Island) supplemented with 9% dialyzed fetal calf serum, 2 mM glutamine, 100 units/ml penicillin and 100 μg/ml streptomycin. Colonies arising from transfected cells were picked using cloning cylinders, expanded and checked for the expression of decorin by immunoprecipitation from $^{35}SO_4$-labeled culture supernatants. Clones expressing a substantial amount of decorin were then subjected to gene amplification by stepwise increasing concentration of methotrexate (MTX) up to 0.64 μM (Kaufman and Sharp, J. Mol. Biol. 159: 601 (1982), which is incorporated herein by reference). All the amplified cell lines were cloned either by limiting dilution or by picking single MTX resistant colonies. Stock cultures of these established cell lines were kept in MTX-containing medium. Before use in protein production, cells were subcultured in MTX-minus medium from stock cultures and passed at least once in this medium to eliminate the possible MTX effects.

Alternatively, the core protein was expressed in COS-1 cells as described in Adams and Rose, Cell 41: 1007, (1985), which is incorporated herein by reference. Briefly, 6-well multiwell plates were seeded with 3-5x105 cells per 9.6 $cm^2$ growth area and allowed to attach and grow for 24 hours. Cultures were transfected with plasmid DNA when they were 50–70% confluent. Cell layers were washed briefly with Tris buffered saline (TBS) containing 50 mM Tris, 150 mM NaCl pH 7.2, supplemented with 1 mM $CaCl_2$ and 0.5 mM $MgCl_2$ at 37° C. to prevent detachment. The wells were incubated for 30 minutes at 37° C. with 1 ml of the above solution containing 2 μg of closed circular plasmid DNA and 0.5 mg/ml DEAE-Dextran (Sigma) of average molecular mass of 500,000. As a control, cultures were transfected with the pSV2 expression plasmid lacking any decorin insert or mock transfected with no DNA. Cultures were then incubated for 3 hours at 37° C. with Dulbecco's Modified Eagle's medium (Irvine Scientific) containing 10% fetal calf serum and 100 μM chloroquine (Sigma), after removing the DNA/TBS/DEAE-Dextran solution and rinsing the wells with TBS. The cell layers were then rinsed twice and cultured in the above medium, lacking any chloroquine, for approximately 36 hours. WI38 human embryonic lung fibroblasts were routinely cultured in the same medium.

COS-1 cultures were radiolabeled 36–48 hours after transfection with the plasmid DNAs. All radiolabeled metabolic precursors were purchased from New England Nuclear (Boston, Mass.). The isotopes used were $^{35}$S-sulfate (460 mCi/ml), L-[3,4,5-$^3$H(N)]-leucine (140 Ci/ml) and L-[$^{14}$C (U)]—amino acid mixture (product number 445E). Cultures were labeled for 24 hours in Ham's F-12 medium (GIBCO Labs), supplemented with 10% dialyzed fetal calf serum, 2 mM glutamine and 1 mM pyruvic acid, and containing 200 μCi/ml $^{35}$S-sulfate or $^3$H-leucine, or 10 μCi/ml of the $^{14}$C-amino acid mixture. The medium was collected, supplemented with 5 mM EDTA, 0.5 mM phenylmethylsulfonylfluoride, 0.04 mg/ml aprotinin and 1 μg/ml pepstatin to inhibit protease activity, freed of cellular debris by centrifugation for 20 minutes at 2,000×G and stored at –20° C. Cell extracts were prepared by rinsing the cell layers with TBS and then scraping with a rubber policeman into 1 ml/well of ice cold cell lysis buffer: 0.05M Tris-HCl, 0.5M NaCl, 0.1% BSA, 1% NP-40, 0.5% Triton X-100, 0.1% SDS, pH 8.3. The cell extracts were clarified by centrifugation for 1.5 hours at 13,000×G at 4° C.

Rabbit antiserum was prepared against a synthetic peptide based on the first 15 residues of the mature form of the human decorin core protein (Asp-Glu-Ala-Ser-Gly-Ile-Gly-Pro-Glu-Val-Pro-Asp-Asp-Arg-Asp). The synthetic peptide and the antiserum against it have been described elsewhere (Krusius and Ruoslahti, 1986 supra.) Briefly, the peptide was synthesized with a solid phase peptide synthesizer (Applied Biosystems, Foster City, Calif.) by using the chemistry suggested by the manufacturer. The peptide was coupled to keyhole limpet hemocyanin by using N-succinimidyl 3-(2-pyridyldithio) propionate (Pharmacia Fine Chemicals, Piscataway, N.J.) according to the manufacturer's instructions. The resulting conjugates were emulsified in Freund's complete adjuvant and injected into rabbits. Further injections of conjugate in Freund's incomplete adjuvant were given after one, two and three months. The dose of each injection was equivalent to 0.6 mg of peptide. Blood was collected 10 days after the third and fourth injection. The antisera were tested against the glutaraldehyde-cross linked peptides and isolated decorin in ELISA (Engvall, Meth. Enzymol. 70: 419–439 (1980)), in immunoprecipitation and immunoblotting, and by staining cells in immunofluorescence, as is well known in the art.

Immunoprecipitations were performed by adding 20 μl of antiserum to the conditioned medium or cell extract collected from duplicate wells and then mixing overnight at 4° C. Immunocomplexes were isolated by incubations for 2 hours at 4° C. with 20 μl of packed Protein A-agarose (Sigma). The beads were washed with the cell lysis buffer, with three tube changes, and then washed twice with phosphate-buffered saline prior to boiling in gel electrophoresis sample buffer containing 10% mercaptoethanol. Immunoprecipitated proteins were separated by SDS-PAGE in 7.5–20% gradient gels or 7.5% non-gradient gels as is well known in the art. Fluorography was performed by using Enlightning (New England Nuclear) with intensification screens. Typical exposure times were for 7–10 days at –70° C. Autoradiographs were scanned with an LKB Ultroscan XL Enhanced Laser Densitometer to compare the relative intensities and mobilities of the proteoglycan bands.

SDS-PAGE analysis of cell extracts and culture medium from COS-1 cells transfected with the decorin-pSV2 construct and metabolically radiolabeled with $^{35}$S-sulfate revealed a sulfated band that was not present in mock-transfected cells. Immunoprecipitation with the antiserum raised against a synthetic peptide derived from the decorin core protein showed that the new band was decorin.

Expression of the construct mutated such that the serine residue which is normally substituted with a glycosaminoglycan (serine-4) was replaced by a threonine residue by SDS-PAGE revealed only about 10% of the level of proteoglycan obtained with the wild-type construct. The rest of the immunoreactive material migrated at the position of free core protein.

The alanine-mutated cDNA construct when expressed and analyzed in a similar manner yielded only core protein and no proteoglycan form of decorin. FIGS. 1A and 1B show the expression of decorin (lanes 1) and its threonine-4 (lanes 3) and alanine-4 (lanes 2) mutated core proteins expressed in COS cell transfectants. $^{35}SO_4$-labeled (FIG. 1A) and $^3$H-leucine labeled (FIG. 1B) culture supernatants were immunoprecipitated with rabbit antipeptide antiserum prepared against the $NH_2$-terminus of human decorin.

Purification of Decorin and Decorin Core Protein from Spent Culture Media

Cells transfected with pSV2-decorin vector and amplified as described above and in Yamaguchi and Ruoslahti, Nature 36: 244–246 (1988), which is incorporated herein by reference, were grown to 90% confluence in 8 175 $cm^2$ culture flasks in nucleoside minus α-MEM supplemented with 9% dialyzed fetal calf serum, 2 mM glutamine, 100 units/ml penicillin and 100 μg/ml streptomycin. At 90% confluence culture media was changed to 25 ml per flask of nucleoside-free α-MEM supplemented with 6% dialyzed fetal calf serum which had been passed through a DEAE Sepharose Fast Plow column (Pharmacia) equilibrated with 0.25M NaCl in 0.05M phosphate buffer, pH 7.4. Cells were cultured for 3 days, spent media was collected and immediately made to 0-5mM phenylmethylsulfonyl fluoride, 1 μg/ml pepstatin, 0.04 mg/ml aprotinin and 5 mM EDTA.

Four hundred milliliters of the spent media were first passed through gelatin-Sepharose to remove fibronectin and materials which would bind to Sepharose. The flow-through fraction was then mixed with DEAE-Sepharose pre-equilibrated in 50 mM Tris/HCl, pH 7.4, plus 0.2M NaCl and batch absorbed overnight at 4° C. with gentle mixing. The slurry was poured into a 1.6×24 cm column, washed extensively with 50 mM Tris/HCl, pH 7.4, containing 0.2M NaCl and eluted with 0.2M-0.8M linear gradient of NaCl in 50 mM Tris/HCl, pH 7.4. Decorin concentration was determined by competitive ELISA as described in Yamaguchi and Ruoslahti, supra. The fractions containing decorin were pooled and further fractionated on a Sephadex gel filtration column equilibrated with 8M urea in the Tris-HCl buffer. Fractions containing decorin were collected.

The core protein is purified from cloned cell lines transfected with the pSV2-decorin/CP vector or the vector containing the alanine-mutated cDNA and amplified as described above. These cells are grown to confluency as described above. At confluency the cell monolayer is washed four times with serum-free medium and incubated in α MEM supplemented with 2 mM glutamine for 2 hours. This spent medium is discarded. Cells are then incubated with α MEM supplemented with 2 mM glutamine for 24 hours and the spent media are collected and immediately made to 0.5 mM phenylmethylsulfonyl fluoride, 1 μg/ml pepstatin, 0.04 mg/ml aprotinin and 5 mM EDTA as serum-free spent media. The spent media are first passed through gelatin-Sepharose and the flow-through fraction is then batch-absorbed to CM-Sepharose Fast Flow (Pharmacia Fine Chemicals, Piscataway, N.J.) pre-equilibrated in 50 mM Tris/HCl, pH 7.4 containing 0.1M NaCl. After overnight incubation at 4° C., the slurry is poured into a column, washed extensively with the pre-equilibration buffer and eluted with 0.1M-1M linear gradient of NaCl in 50 mM Tris/HCl, pH 7.4. The fractions containing decorin are pooled, dialyzed against 50 mM NH$_4$HCO$_3$ and lyophilized. The lyophilized material is dissolved in 50 mM Tris, pH 7.4, containing 8M urea and applied to a Sephacryl S-200 column (1.5×110 cm). Fractions containing decorin core proteins as revealed by SDS-polyacrylamide electrophoresis are collected and represent purified decorin core protein.

EXAMPLE II

BINDING OF TGF-β TO DECORIN a. Affinity Chromatoqraphy of TGF-β on Decorin-Sepharose Decorin and gelatin were coupled to cyanogen bromide-activated Sepharose (Sigma) by using 1 mg of protein per ml of Sepharose matrix according to the manufacturer's instructions. Commercially obtained TGF-B1 (Calbiochem, La Jolla, Calif.) was $^{125}$I-labelled by the chloramine T method (Frolik et al., J. Biol. Chem. 259: 10995–11000 (1984)) which is incorporated herein by reference and the labeled TGF-β was separated from the unreacted iodine by gel filtration on Sephadex G-25, equilibrated with phosphate buffered saline (PBS) containing 0.1% bovine serum albumin (BSA) (FIG. 2). [$^{125}$I]-TGF-β1 (5×10$^5$ cpm) was incubated in BSA-coated polypropylene tubes with 0.2 ml of packed decorin-Sepharose (●) or gelatin-Sepharose (○) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer. Fractions were collected, counted for radioactivity in a gamma counter and analyzed by SDS-PAGE under nonreducing condition using 12% gels.

FIG. 2A shows the radioactivity profile from the two columns and the SDS-PAGE analysis of the fractions is shown in FIG. 2B. The TGF-β1 starting material contains a major band at 25 kd. This band represents the native TGF-β1 dimer. In addition, there are numerous minor bands in the preparation. About 20–30% of the radioactivity binds to the decorin column and elutes with 8M urea, whereas only about 2% of the radioactivity is present in the urea-eluted fraction in the control fractionation performed on gelatin-Sepharose (FIG. 2A). The decorin-Sepharose nonbound fraction contains all of the minor components and some of the 25 kd TGF-β1, whereas the bound, urea-eluted fraction contains only TGF-β1 (FIG. 2B). These results show that TGF-β1 binds specifically to decorin, since among the various components present in the original TGF-β1 preparation, only TGF-β1 bound to the decorin-Sepharose affinity matrix and since there was very little binding to the control gelatin-Sepharose affinity matrix. The TGF-β1 that did not bind to the decorin-Sepharose column may have been denatured by the iodination. Evidence for this possibility was provided by affinity chromatography of unlabeled TGF-β1 as described below.

In a second experiment, unlabeled TGF-β1 180 ng was fractionated on decorin-Sepharose as described above for $^{125}$I-TGF-β.

TGF-β1 (180 ng) was incubated with decorin-Sepharose or BSA-agarose (0.2 ml packed volume) in PBS (pH 7.4) containing 1% BSA. After overnight incubation at 4° C., the resins were washed with 15 ml of the buffer and eluted first with 5 ml of 3M NaCl in PBS then with 5 ml of PBS containing 8M urea. Aliquots of each pool were dialyzed against culture medium without serum and assayed for the inhibition of [$^3$H]thymidine incorporation in MvLu cells (Example III). The amounts of TGF-β1 in each pool were calculated from the standard curve of [$^3$H]thymidine incorporation obtained from a parallel experiment with known concentration of TGF-β1. The results show that the TGF-β1 bound essentially quantitatively to the decorin column, whereas there was little binding to the control column (Table 1). The partial recovery of the TGF-β1 activity may be due to loss of TGF-β1 in the dialyses.

TABLE I

Decorin-Sepharose affinity chromatography of nonlabeled TGF-β1 monitored by growth inhibition assay in MvLu cells.

| | TGF-β1 (ng) | |
|---|---|---|
| Elution | Decorin-Sepharose | BSA-Sepharose |
| Flow through & wash | 2.7 (2.3%) | 82.0 (93.9%) |
| 3 M NaCl | 2.2 (1.8%) | 1.3 (1.5%) |
| 8 M Urea | 116.0 (95.9%) | 4.0 (4.6%) | b. Binding of TGF-β1 to Decorin in a Microtiter Assay: Inhibition by Core Protein and Biglycan The binding of TGF-β1 to decorin was also examined in a microtiter binding assay. To perform the assay, the wells of a 96-well microtiter plate were coated overnight with 2

μg/ml of recombinant decorin in 0.1M sodium carbonate buffer, pH 9.5. The wells were washed with PBS containing 0.05% Tween (PBS/Tween) and samples containing 5×10$^4$ cpm of [$^{125}$I]-TGF-β1 and various concentrations of competitors in PBS/Tween were added to each well. The plates were then incubated at 37° C. for 4 hours (at 4° C. overnight in experiments with chondroitinase ABC-digested proteoglycans), washed with PBS/Tween and the bound radioactivity was solubilized with 1% SDS in 0.2M NaOH. Total binding without competitors was about 4% under the conditions used. Nonspecific binding, determined by adding 100-fold molar excess of unlabeled TGF-β1 over the labeled TGF-β1 to the incubation mixture, was about 13% of total binding. This assay was also used to study the ability of other decorin preparations and related proteins to compete with the interaction.

Completion of the decorin binding was examined with the following proteins (FIGS. 3A–13B; symbols are indicated in the section of BRIEF DESCRIPTION OF THE FIGURES): (1) Decorin isolated from bovine skin (PGII), (2) biglycan isolated from bovine articular cartilage (PGI) (both PGI and PGII were obtained from Dr. Lawrence Rosenberg, Monteflore Medical Center, N.Y.; and described in Rosenberg et al., J. Biol. Chem. 250: 6304–6313, (1985), incorporated by reference herein), and (3) chicken cartilage proteoglycan (provided by Dr. Paul Goetinck, La Jolla Cancer Research Foundation, La Jolla, Calif., and described in Goetinck, P. F., in *The Glycoconjugates*, Vol. III, Horwitz, M. I., Editor, pp. 197–217, Academic Press, N.Y.).

Figure 3B:
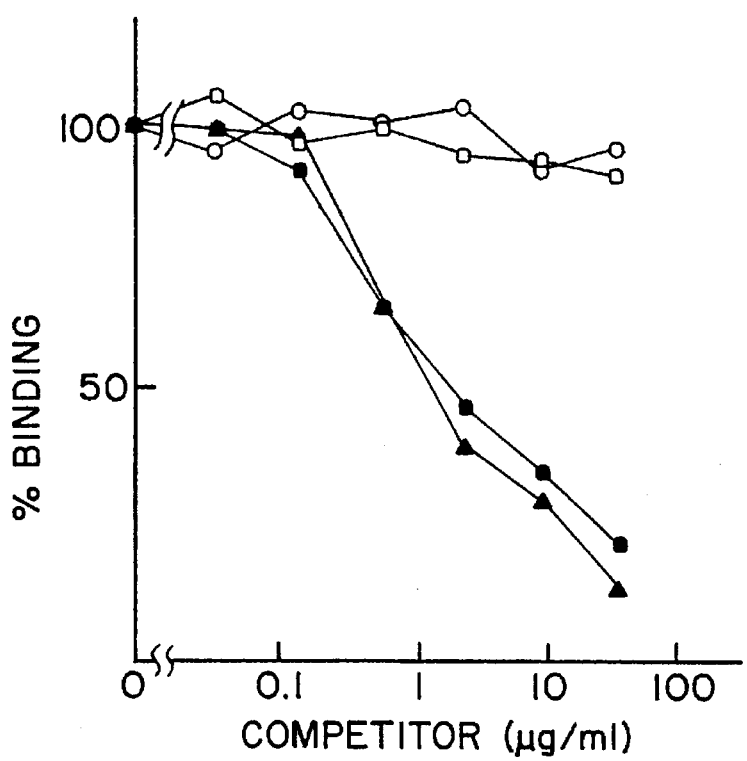

For the preparation of core proteins, proteoglycans were digested with chondroitinase ABC (Seikagaku, Tokyo, Japan) by incubating 500 μg of proteoglycan with 0.8 units of chondroitinase ABC in 250 μl of 0.1M Tris/Cl, pH 8.0, 30 mM sodium acetate, 2 mM PMSF, 10 mM N-ethylmalelmide, 10 mM EDTA, and 0.36 mM pepstatin for 1 hour at 37° C. Recombinant decorin and decorin isolated from bovine skin (PGII) inhibited the binding of [$^{125}$I]-TGF-β1, as expected (FIG. 3A). Biglycan isolated from bovine articular cartilage was as effective an inhibitor as decorin. Since chicken cartilage proteoglycan, which carries many chondroitin sulfate chains, did not show any inhibition, the effect of decorin and biglycan is unlikely to be due to glycosaminoglycans. Bovine serum albumin did not shown any inhibition. This notion was further supported by competition experiments with the mutated decorin core protein (not shown) and chondroitinase ABC-digested decorin and biglycan (FIG. 3B). Each of these proteins was inhibitory, whereas cartilage proteoglycan core protein was not. The decorin and biglycan core proteins were somewhat more active than the intact proteoglycans. Bovine serum albumin treated with chondroitinase ABC did not shown any inhibition. Additional binding experiments showed that [$^{125}$I]-TGF-β1 bound to microtiter wells coated with biglycan or its chondroitinase-treated core protein. These results show that TGF-β1 binds to the core protein of decorin and biglycan and implicates the leucine-rich repeats these proteins share as the potential binding sites.

EXAMPLE III

ANALYSIS OF THE EFFECT OF DECORIN ON CELL PROLIFERATION STIMULATED OR INHIBITED BY TGF-β1

Figure 4A:
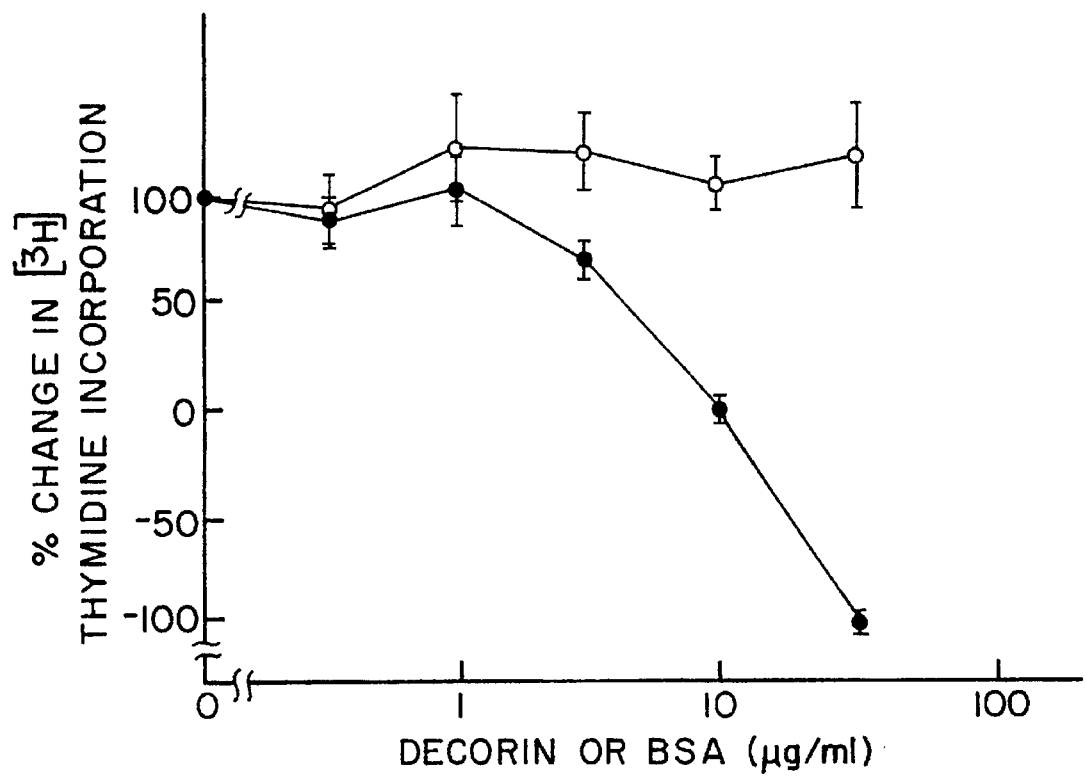
FIGS. 4A and 4B show neutralization of the growth regulating activity of TGF-β1 by decorin.

The ability of decorin to modulate the activity of TGF-β1 was examined in [$^3$H]thymidine incorporation assays. In one assay, an unamplified CHO cell line transfected only with pSV2dhfr (control cell line A in reference 1, called CHO cells here) was used. The cells were maintained in nucleoside-free alpha-modified minimal essential medium (α-MEM, GIBCO, Long Island, N.Y.) supplemented with 9% dialyzed fetal calf serum (dFCS) and [$^3$H]thymidine incorporation was assayed as described (Cheifetz et al., Cell 48: 409–415 (1987)). TGF-β1 was added to the CHO cell cultures at 5 ng/ml. At this concentration, it induced a 50% increase of [$^3$H]thymidine incorporation in these cells. Decorin or BSA was added to the medium at different concentrations. The results are shown in FIG. 4A. The data represent percent neutralization of the TGF-β1-induced growth stimulation, i.e., [$^3$H]thymidine incorporation, in the absence of either TGF-β1 or decorin=0%, incorporation in the presence of TGF-β1 but not decorin=100%. Each point shows the mean ±standard deviation of triplicate samples. Decorin (●) BSA (○).

Decorin neutralized the growth stimulatory activity of TGF-β1 with a half maximal activity at about 5 μg/ml. Moreover, additional decorin suppressed the [$^3$H]-thymidine incorporation below the level observed without any added TGF-β1, demonstrating that decorin also inhibited TGF-β made by the CHO cells themselves. Both the decorin-expressor and control CHO cells produced an apparently active TGF-β concentration of about 0.25 ng/ml concentration into their conditioned media as determined by the inhibition of growth of the mink lung epithelial cells. (The assay could be performed without interference from the decorin in the culture media because, as shown below, the effect of TGF-β on the mink cells was not substantially inhibited at the decorin concentrations present in the decorin-producer media.)

Figure 4B:
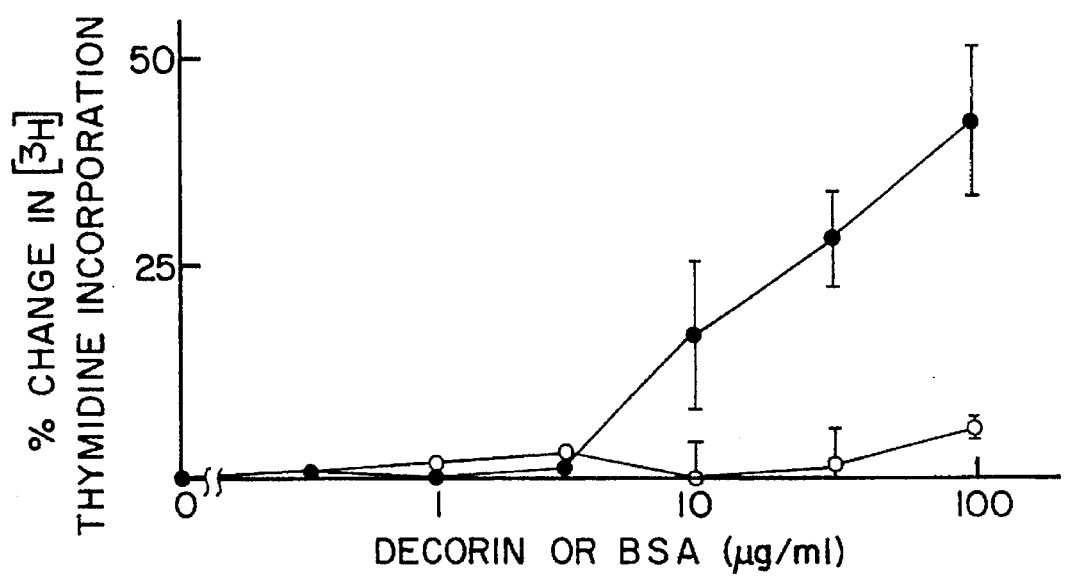

Experiments in MvLu mink lung epithelial cells (American Type Culture Collection CCL 64) also revealed an effect by decorin on the activity of TGF-β1. FIG. 4B shows that in these cells, the growth of which is measured by thymidine incorporation, had been suppressed by TGF-β1. Assay was performed as in FIG. 4A, except that TGF-β1 was added at 0.5 ng/ml. This concentration of TGF-β induces 50% reduction of [$^3$H]-thymidine incorporation in the MvLu cells. The data represent neutralization of TGF-β-induced growth inhibition; i.e., [$^3$H]-thymidine incorporation in the presence of neither TGF-β or decorin=100%; incorporation in the presence of TGF-β but not decorin=0%.

EXAMPLE IV

NEW DECORIN-BINDING FACTOR THAT CONTROLS CELL SPREADING AND SATURATION DENSITY

Analysis of the decorin contained in the overexpressor culture media not only uncovered the activities of decorin described above, but also revealed the presence of other decorin-associated growth regulatory activities. The overexpressor media were found to contain a TGF-β-like growth inhibitory activity. This was shown by gel filtration of the DEAE-isolated decorin under dissociating conditions. Serum-free conditioned medium of decorin overexpressor CHO-DG44 cells transfected with decorin cDNA was fractionated by DEAE-Sepharose chromatography in a neutral Tris-HCl buffer and fractions containing growth inhibitory activity dialyzed against 50 mM NH$_4$HCO$_3$, lyophilized and dissolved in 4M with guanidine-HCl in a sodium acetate buffer, pH 5.9. The dissolved material was fractionated on a 1.5×70 cm Sepharose CL-6B column equilibrated with the same guanidine-HCl solution. The fractions were analyzed by SDS-PAGE, decorin ELISA and cell growth assays, all described above. Three protein peaks were obtained. One contained high molecular weight proteins such as fibronectin (m.w. 500,000) and no detectable growth regulatory activities, the second was decorin with the activities described under Example III and the third was a low molecular weight (10,000–30,000-dalton) fraction that had a growth inhibitory activity in the mink cell assay and stimulated the growth of the CHO cells. FIG. 5 summarizes these results. Shown are the ability of the gel filtration fractions to affect [$^3$H]-thymidine incorporation by the CHO cells and the concentration of decorin as determined by enzyme immunoassay. Shown also (arrows) are the elution positions of molecular size markers: BSA, bovine serum albumin (Mr=66,000); CA, carbonic anhydrase (Mr=29,000); Cy, cytochrome c (Mr=12,400); AP, aprotinin (Mr=6,500); TGF, [$^{125}$I]-TGF-β1 (Mr=25,000).

The nature of the growth regulatory activity detected in the low molecular weight fraction was examined with an anti-TGF-β1 antiserum. The antiserum was prepared against a synthetic peptide from residues 78–109 of the human mature TGF-β1. Antisera raised by others against a cyclic form of the same peptide, the terminal cysteine residues of which were disulfide-linked, have previously been shown to inhibit the binding of TGF-β1 to its receptors (Flanders et al., Biochemistry 27: 739–746 (1988), incorporated by reference herein). The peptide was synthesized in an Applied Biosystems solid phase peptide synthesizer and purified by HPLC. A rabbit was immunized subcutaneously with 2 mg per injection of the peptide which was mixed with 0.5 mg of methylated BSA (Sigma, St. Louis, Mo.) and emulsified in Freund's complete adjuvant. The injections were generally given four weeks apart and the rabbit was bled approximately one week after the second and every successive injection. The antisera used in this work has a titer (50% binding) of 1: 6,000 in radioimmunoassay, bound to TGF-β1 in immunoblots.

Figure 5A:
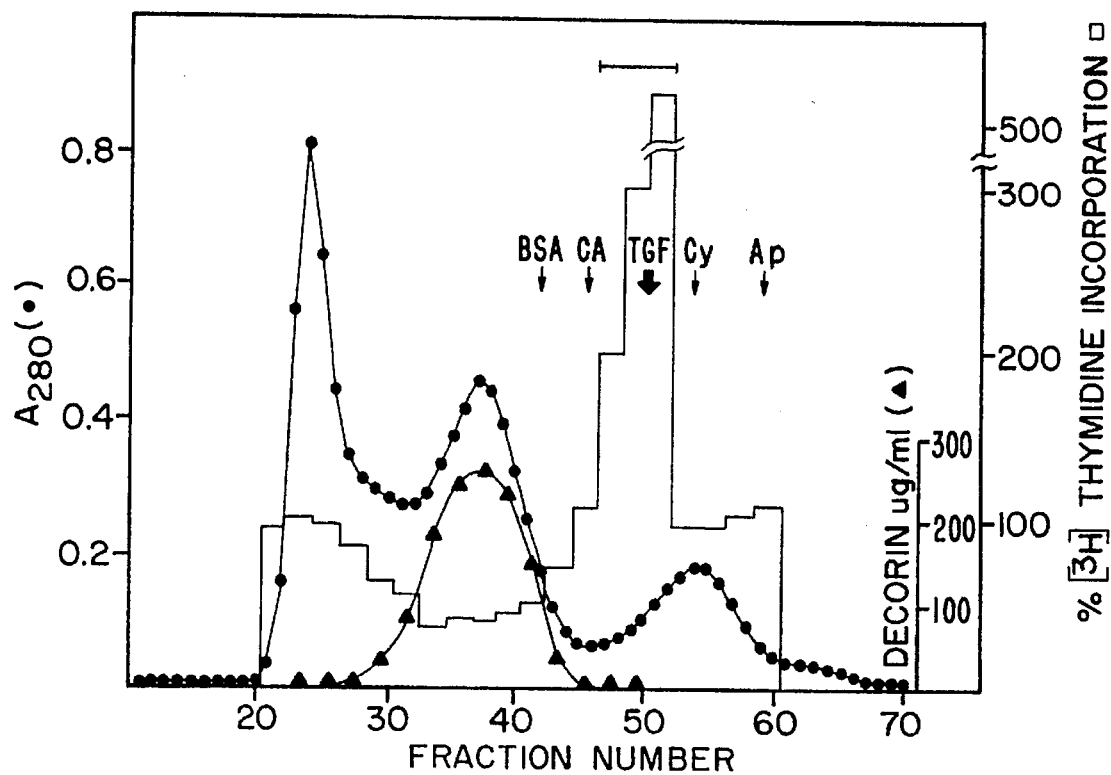
FIG. 5A shows separation of growth inhibitory activity from decorin-expressing CHO cells by gel filtration. Serum-free conditioned medium of decorin overexpressor cells was fractionated by DEAE-Sepharose chromatography in a neutral Tris-HCl buffer and fractions containing growth inhibitory activity were pooled, made 4M with guanidine-HCl and fractionated on a Sepharose CL-6B column equilibrated with the same guanidine-HCl solution. The fractions were analyzed for protein content, decorin content, and growth regulatory activities. Elution positions of marker proteins are indicated by arrows. BSA: bovine serum albumin (Mr= 66,000); CA: carbonic anhydrase (Mr=29,000); Cy: cytochrome c (Mr=12,400); Ap: aprotinin (Mr=6,500); TGF: [$^{125}$I]-TGF-β1 (Mr=25,000).
Figure 5B:
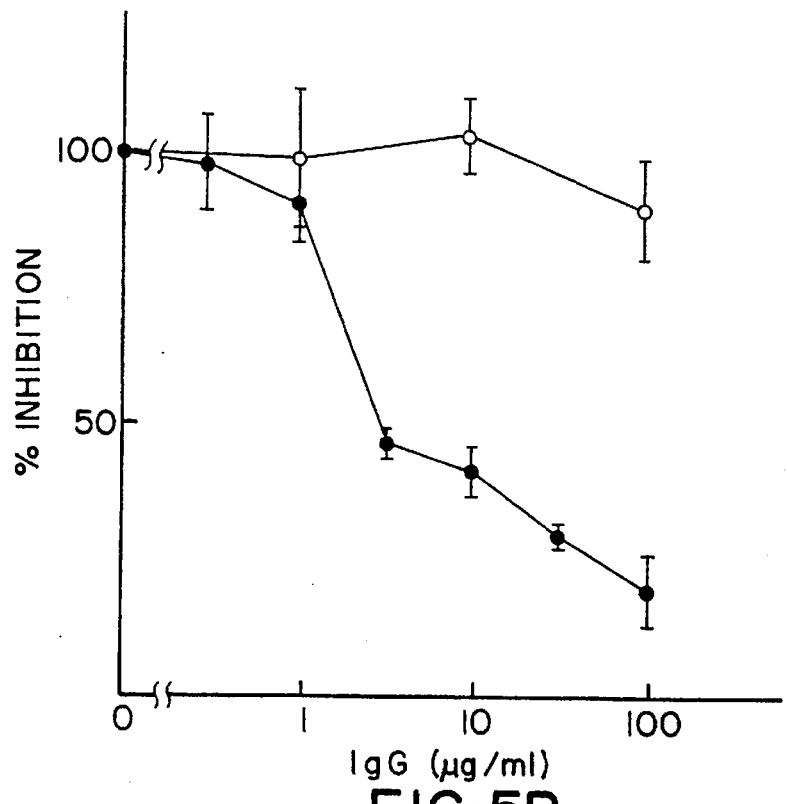
FIG. 5B shows identification of the growth stimulatory material from gel filtration as TGF-β1. The growth stimulatory activity from the late fractions from Sepharose 6B (bar in panel A) was identified by inhibiting the activity with protein A-purified IgG from an anti-TGF-β antiserum. Data represent percent inhibition of growth stimulatory activity in a [$^3$H]thymidine incorporation assay. Each point shows the mean ±standard deviation of triplicate determinations. Anti-TGF-β1 (●), normal rabbit IgG (○).

This antiserum was capable of inhibiting the activity of purified TGF-β1 on the CHO cells. Moreover, as shown in FIG. 5A and 5B, the antiserum also inhibited the growth stimulatory activity of the low molecular weight fraction as determined by the [$^3$H]-thymidine incorporation assay on the CHO cells. Increasing concentrations of an IgG fraction prepared from the anti-TGF-β1 antiserum suppressed the stimulatory effect of the low molecular weight fraction in a concentration-dependent manner (●). IgG from a normal rabbit serum had no effect in the assay (o).

The above result identified the stimulatory factor in the low molecular weight fraction as TGF-β1. However, TGF-β1 is not the only active compound in that fraction. Despite the restoration of thymidine incorporation by the anti-TGF-β1 antibody shown in FIG. 5A and 5B, the cells treated with the low molecular weight fraction were morphologically different from the cells treated with the control IgG or cells treated with antibody alone. This effect was particularly clear when the antibody-treated, low molecular weight fraction was added to cultures of H-ras transformed NIH 3T3 cells (Der et al., Proc. Natl. Acad. Sci. USA 79: 3637–3640 (1982)). As shown in FIGS. 6A and 6B, cells treated with the low molecular weight fraction and antibody (micrograph in FIG. 6B) appeared more spread and contact inhibited than the control cells (micrograph in FIG. 6A). This result shows that the CHO cell-derived recombinant decorin is associated with a cell regulatory factor, MRF, distinct from the well characterized TGF-β's.

Additional evidence that the new factor is distinct from TGF-β1 came from HPLC experiments. Further separations of the low molecular weight from the Sepharose CL-6B column was done on a Vydac C4 reverse phase column (1×25 cm, 5 μm particle size, the Separations Group, Hesperia, Calif.) in 0.1% trifluoroacetic acid. Bound proteins were eluted with a gradient of acetonitrite (22–40%) and the factions were assayed for growth-inhibitory activity in the mink lung epithelial cells and MRF activity in H-ras 3T3 cells. The result showed that the TGF-β1 activity eluted at the beginning of the gradient, whereas the MRF activity eluted toward the end of the gradient.

EXAMPLE V

INHIBITION OF TGF-β BINDING

A. Cross Linking of [$^{125}$I]-TGF-β to HepG2 Cells

About 2.5×10$^4$ HepG2 cells (human hepatocellular carcinoma, ATCC No. HB 8065) were incubated with 100 pM [$^{125}$I]-TGF-β in the presence of recombinant decorin, TGF-β, or α-TGF-β antibody for 2 hours at room temperature. Cells were washed four times prior to suspension in binding buffer (128 mM NaCl, 5 mM KCl, 5 mM Mg$_2$SO$_4$, 1.2 mM CaCl$_2$, 50 mM HEPES, 2 mg/ml BSA, pH 7.5) containing 0.25 mM disuccinimidyl suberate (DSS) for 15 minutes. Cells were subsequently washed in washing buffer (binding buffer without BSA) containing 150 mM sucrose and lysed before suspension in Laemmli sample buffer, which is known to those skilled in the art, containing SDS. The lysates were resolved on 4–12% SDS-PAGE under reducing and non-reducing conditions. Cross-linked TGF-β was visualized by autoradiography.

Figure 7A:
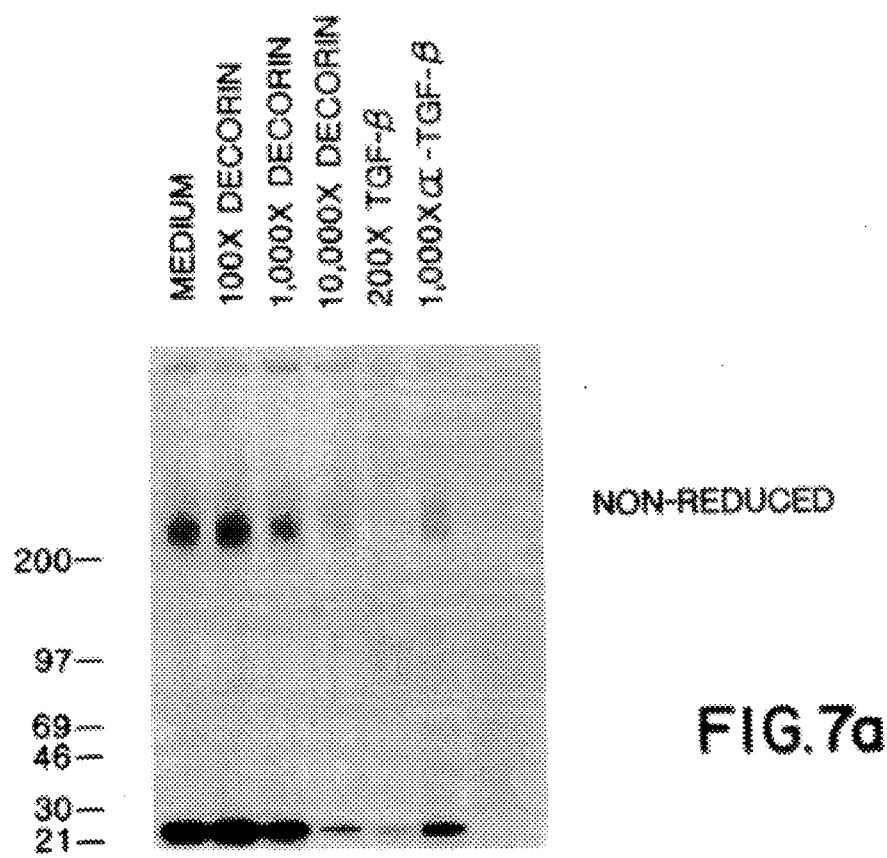
FIGS. 7A and 7B show that decorin inhibits the binding of [$^{125}$I]-TGF-β to Type III TGF-β receptor (β glycan) on HepG2 cells.
Figure 7B:
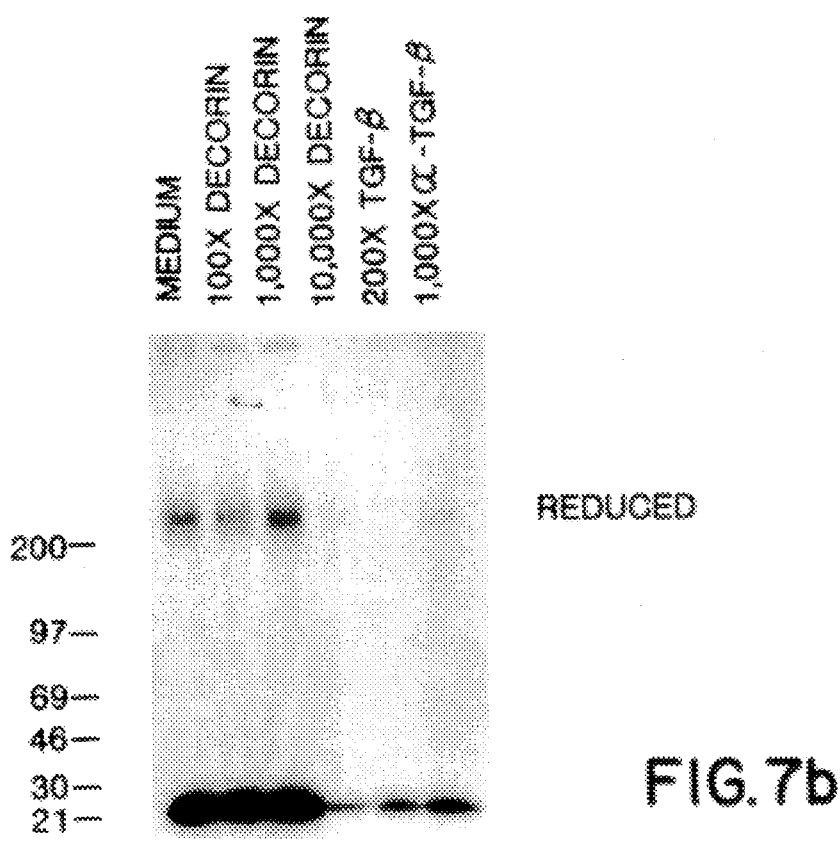

FIGS. 7A and 7B show the results of the studies. Decorin inhibits the binding of TGF-β to β glycan, a TGF-β receptor found on HepG2 cells.

B. Cross Linking of [$^{125}$I]-TGF-β to MG-63 Cells

About 10$^5$ MG-63 cells (male osteosarcoma, ATCC No. CRL 1427) were incubated with 150 pM [$^{25}$I]-TGF-β in the presence of a recombinant decorin preparation (designated as DC-13) or TGF-β for 2 hours at room temperature. Cells were washed four times in ice cold binding buffer of Example V(A) prior to suspension in binding buffer containing 0.25 mM DSS for 15 minutes. Cells were washed in 250 mM sucrose buffer before lysis in 1% Triton X-100 buffer, containing protease inhibitors. Lysed cells were centrifuged at 12,000×g to remove nuclei. Equivalent volumes of Laemmli SDS sample buffer were added to each supernatant prior to electrophoresis through 4–12% tris-glycine gels. The cross-linked TGF-225 was visualized by autoradiography.

Figure 8A:
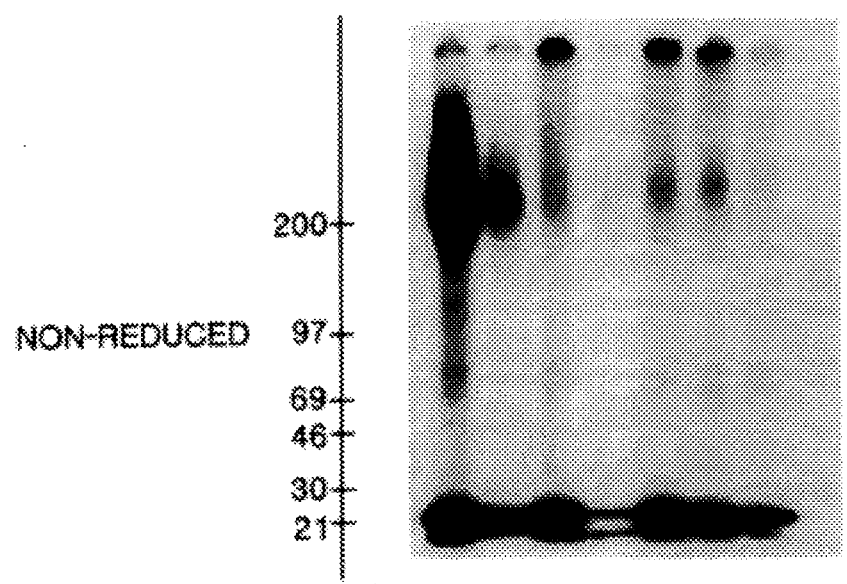
FIGS. 8A and 8B show that decorin inhibits the binding of [$^{125}$I]-TGF-β to Type III TGF-β receptor on MG-63 cells.
Figure 8B:
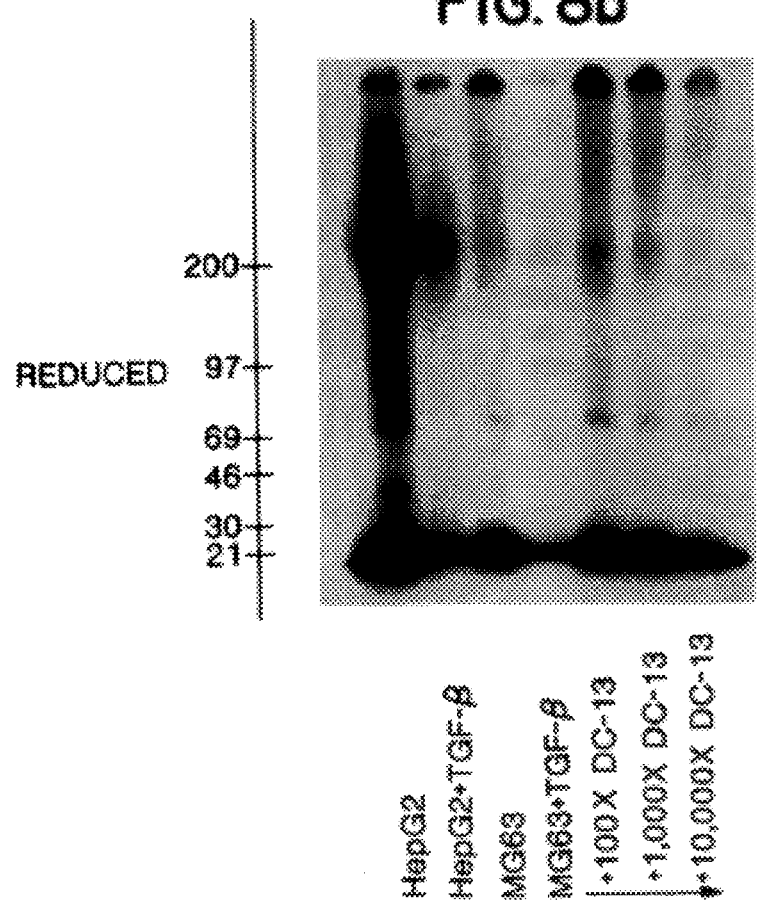
Figure 9:
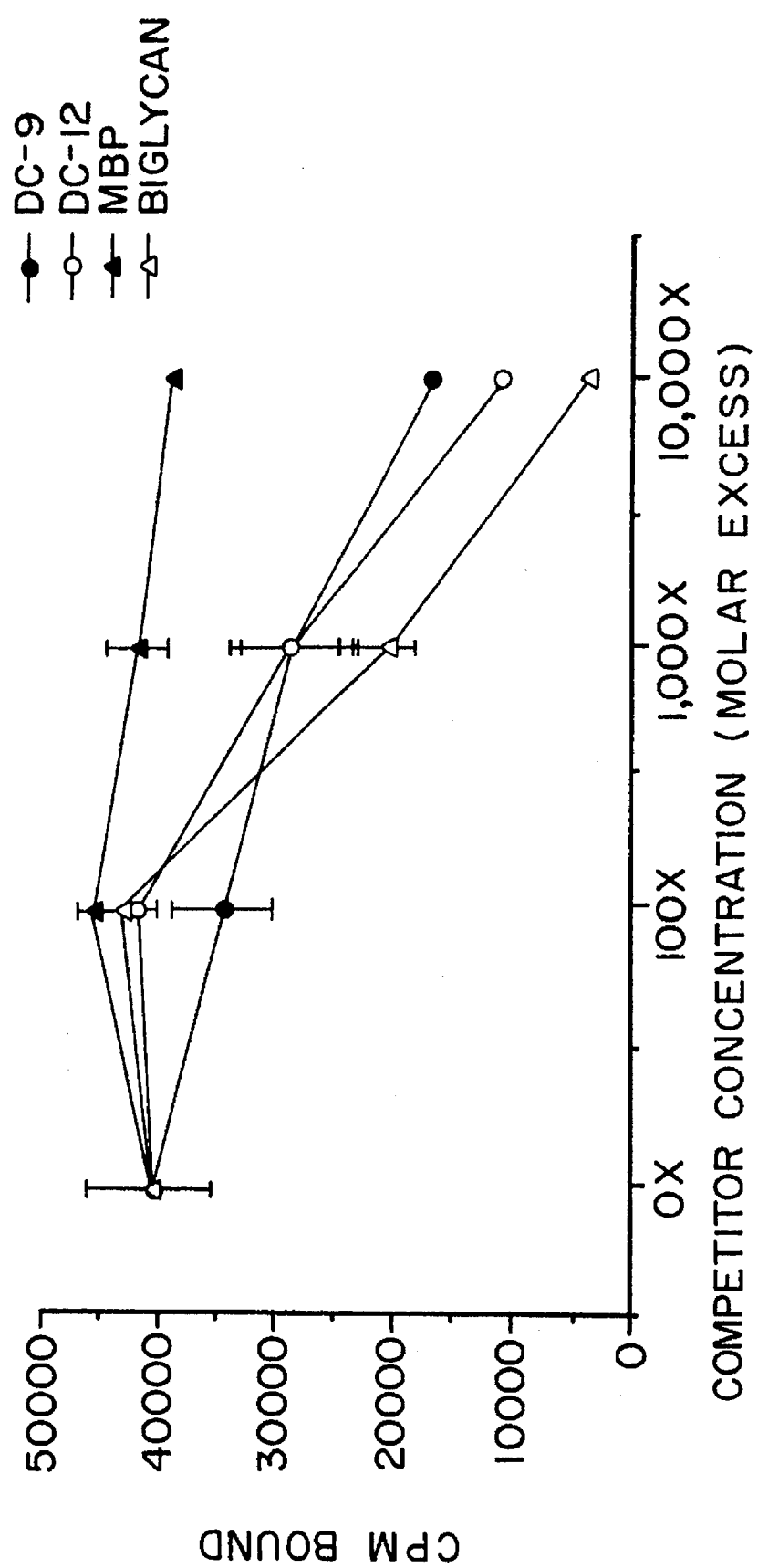

FIGS. 8A and 8B show the results of the studies. Similar to the above studies with HepG2 cells, decorin also inhibits TGF-β binding to its receptors on the MG-63 cells.

C. Binding Studies of $^{125}$I-TGF-β to Immobilized Decorin

A 96-well Linbro microtiter plate was coated with 0.5 μg/ml recombinant decorin at 50 μl/well. The plate was placed in a 37° C. incubator overnight and thereafter washed 3 times with 200 μl PBS (0.15M NaCl) per well to remove unbound decorin. TGF-β labeled with $^{125}$I (400 pM, New England Nuclear, Bolton-Hunter Labeled) was pre-incubated with or without competitors in 200 μl PBS/0.05% Tween-20 for 1 hour, 45 minutes at room temperature. Competitors included recombinant human decorin preparations (DC-9 and DC-12) and biglycan, with MBP as a negative control. DC-9 and DC-12 are different preparations of recombinant human decorin; PT-71 or MBP (maltose-binding protein) is a negative control; and biglycan is recombinant human biglycan.

Fifty μl/well of the pre-incubated TGF-β mixture or control were added and incubated overnight at 0° C. Following the incubation, 50 µl of the free TGF-β supernatants were transferred to labeled tubes. The plate was washed 3 times with 0.05% Tween-20 in PBS (200 µl/well). Reducing sample buffer (2X Laemmli sample buffer) was added at 100 µl/well and incubated at 37° C. for 30 minutes. While gently pulsing the solution, 100 µl of bound $^{125}$I-TGF-β was removed from each well and transferred into tubes for counting in a gamma counter. The 50 µl free TGF-β samples were counted in parallel to the 100 µl bound TGF-β samples to obtain the bound: free ratio. The results of the binding studies with immobilized decorin are summarized in FIG. 9.

D. Binding of $^{125}$I-TGF-β to HepG2 Cells

About 2.5×10$^4$ HepG2 cells were incubated with 250 pM [$^{125}$I]-TGF-β, in the presence of recombinant human decorin (DC-12) or PT-71 (MBP) for 2 hours at room temperature. Cells were washed with the washing buffer of Example V(A) four times before determination of bound CPM.

The results are summarized in FIG. 10. Table II provides numerical data for decorin (DC-12) inhibition of TGF-β binding to HepG2 cells. The "% Change" represents the difference in the mean cpm of the test samples compared to the cpm of the medium (negative control). The α-TGF-β antibody inhibits the binding of labeled TGF-β to cells bearing TGF-β receptors and serves as a positive control.

TABLE II

BINDING OF 125I-TGF-β1 TO HEPG2 CELLS

| Treatment | CPM Concentration | Bound | Mean | % Change |
|---|---|---|---|---|
| Medium* | — | 13,899** | | |
| | | 13,898 | | |
| | | 12,529 | | |
| | | 11,764 | | |
| | | 12,694 | | |
| | | 12,448 | 12,872 ± 856 | — |
| TGP-β1 | 2.5 × 10E-8M | 3,092 | | |
| | | 2,543 | | |
| | | 2,800 | 2,812 ± 275 | −78 |
| Anti-TGF-β1 (R&D) | 2.5 × 10E-7M | 6,191 | | |
| | | 4,848 | | |
| | | 3,839 | 4,959 ± 1,180 | −61 |
| Decorin (DC-12) | 2.5 × 10E-6M | 2,745 | | |
| | | 2,844 | | |
| | | 1,945 | 2,511 ± 493 | −80 |
| | 2.5 × 10E-7M | 4,258 | | |
| | | 5,914 | | |
| | | 4,052 | 4,741 ± 1,021 | −63 |
| | 2.5 × 10E-8M | 13,596 | | |
| | | 12,798 | | |
| | | 11,599 | 12,664 ± 1,005 | −2 |
| PT-71 | 2.5 × 10E-6M | 11,859 | | |
| | | 13,129 | | |
| | | 12,348 | 12,449 ± 636 | −3 |
| | 2.5 × 10E-7M | 11,259 | | |
| | | 11,022 | | |
| | | 9,343 | 10,541 ± 1,045 | −18 |
| | 2.5 × 10E-8M | 10,886 | | |
| | | 10,778 | | |
| | | 10,104 | 10,589 ± 424 | −18 |

*25,000 HepG2 cells obtained from subconfluent cultures were incubated with 250 pM 125I-TGF-β1 and TGF-β, anti TGF-β, decorin, or decorin fragments for 2 hours at room temperature.
**Unbound 125I-TGF-β1 was separated from bound by washing cells 4x.

EXAMPLE VI

SCARRING STUDIES

Adult mice were incised with paired longitudinal wounds on the shaved dorsal skin. Care was taken to cut through the panniculus down to the skeletal musculature of the dorsal skin. The incisions were treated with a 250 µl single dose of either 10 mg/ml hyaluronic acid (control), or a decorin (0.5 mg/ml)/hyaluronic acid (10 mg/ml) mixture in TBS. To form the mixture, 0.5 mg/ml of recombinant decorin was mixed with 10 mg/ml of hyaluronic acid. Each mouse had a blinded control and treated incision. The wounds were sutured closed. Following 14 days, the incisions were monitored grossly and harvested for histology. Frozen sections of the control and treated incision sites (4 microns) were analyzed using standard histological procedures with Massoh's trichrome to visualize the staining.

The hyaluronic acid control exhibited a typical dermal scar as is seen in normal adult animals, whereas the decorin-treated wounds exhibited no detectable scar and were essentially normal histologically. The decorin-treated wounds resembled fetal wounds in the first two trimesters.

EXAMPLE VII

CLONING OF HUMAN BIGLYCAN AND FIBROMODULIN cDNAs

Total cellular RNA was extracted by using guanidinium isothiocyanate (Sambrook et al., 1989) from subconfluent cultures of WI-38 human lung fibroblasts (ATCC Accession No. CCL 75; Rockville, Md.) that had been exposed to TGF-β1 (3 ng/ml) for 12 hours. Total cellular RNA (1 µg) was reverse transcribed with MoMuLV reverse transcriptase using random hexanucleotides for cDNA priming (Kawasaki, 1989). Double-stranded cDNAs encoding the full-length coding sequences of human biglycan or human fibromodulin were generated by amplification of the reverse transcribed WI-38 RNAs using amplimers based on the published sequences of human biglycan (Fisher et al., 1989) or bovine fibromodulin (Oldberg et al., 1989). For decorin, a previously described decorin cDNA was used as a template (Krusius and Ruoslahti, 1986). The PCR products were subcloned into pBluescript (Stratagene, La Jolla, Calif.). The identities of the resulting PCR products were verified by DNA sequencing (Sanger, et al., 1977). The PCR generated biglycan clone differs from the published biglycan sequence in five bases. Two sequence differences could be reconciled by re-sequencing of clone p16 of Fisher et al. (1989), kindly provided by Dr. L. Fisher. The remaining differences resulted in one amino acid exchange ($Lys_{176}$ to $Asn_{176}$).

Figure 11A:
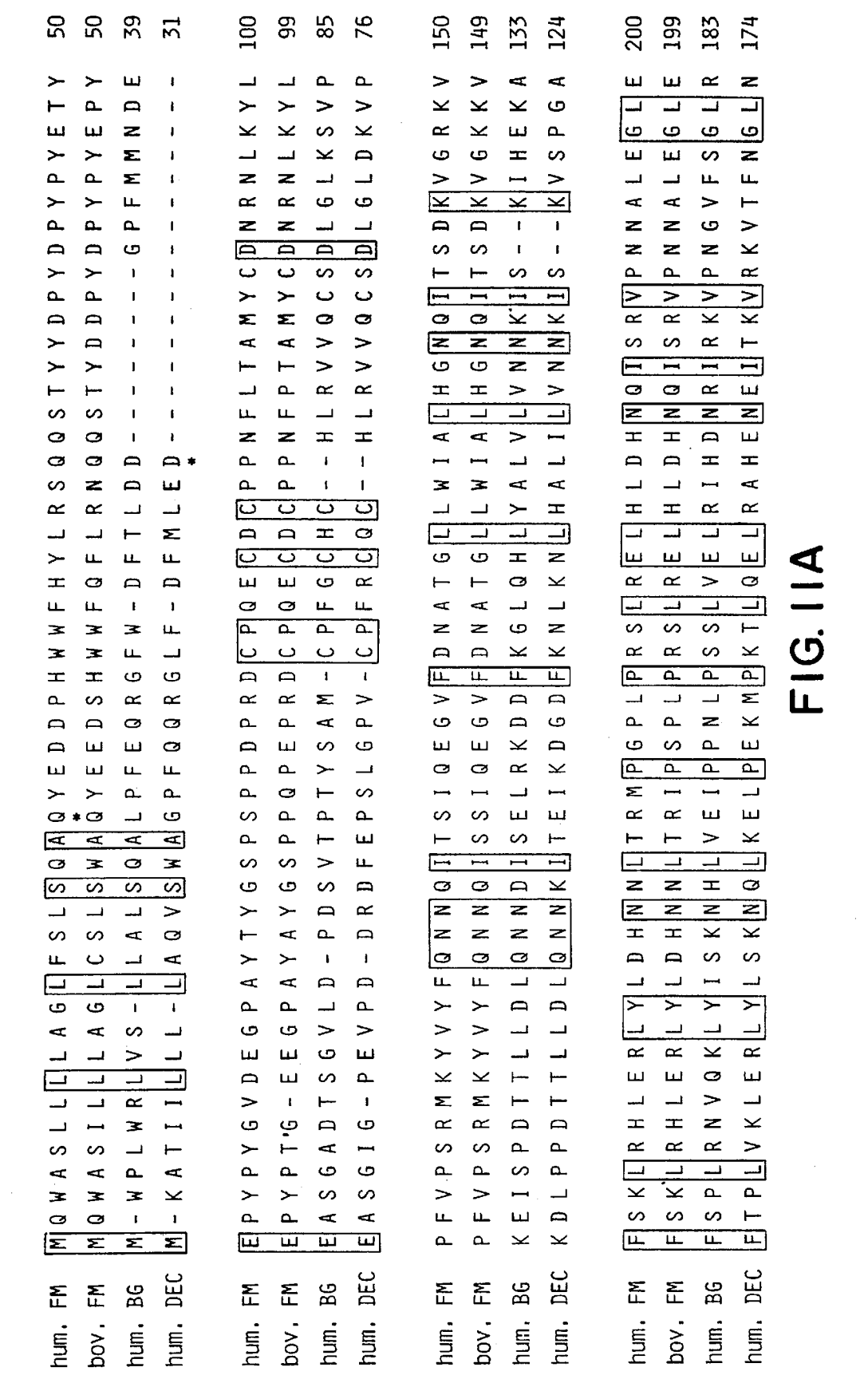
Figure 11B:
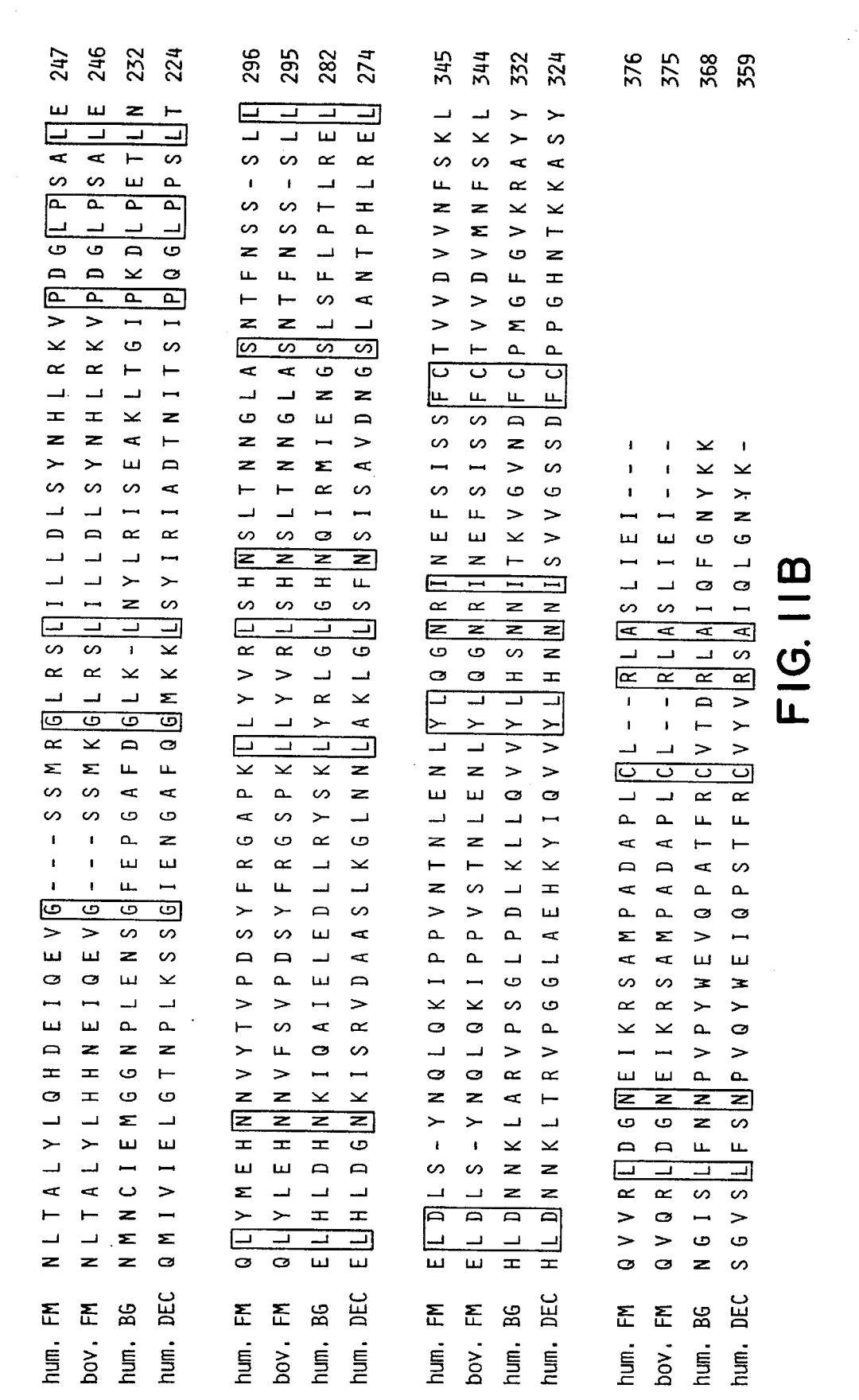

Human fibromodulin was found to be highly homologous to its bovine equivalent. DNA sequencing analysis of the 1.2 kb PCR product revealed a 1128 bp open reading frame that codes for a 376 amino acid protein. The deduced protein sequence shares 92% sequence identity with the previously published bovine fibromodulin sequence. FIG. 11 shows the human fibromodulin amino acid sequence aligned with the bovine fibromodulin sequence and the sequences of the other two proteoglycans used in this study.

EXAMPLE VIII

EXPRESSION VECTOR CONSTRUCTION AND FUSION PROTEIN PURIFICATION

A modified MBP sequence with a COOH-terminal factor Xa-cleavage site was introduced into a vector, pQE-8 (Quiagen; Chatsworth, Calif.), that also encoded an affinity tag consisting of a cassette of six histidines. The pQE-8/MBP expression vector was generated by subcloning the BglII/BamHI DNA fragment coding for MBP and a factor Xa protease cleavage site into the BamHI site of pQE-8

Figure 12:
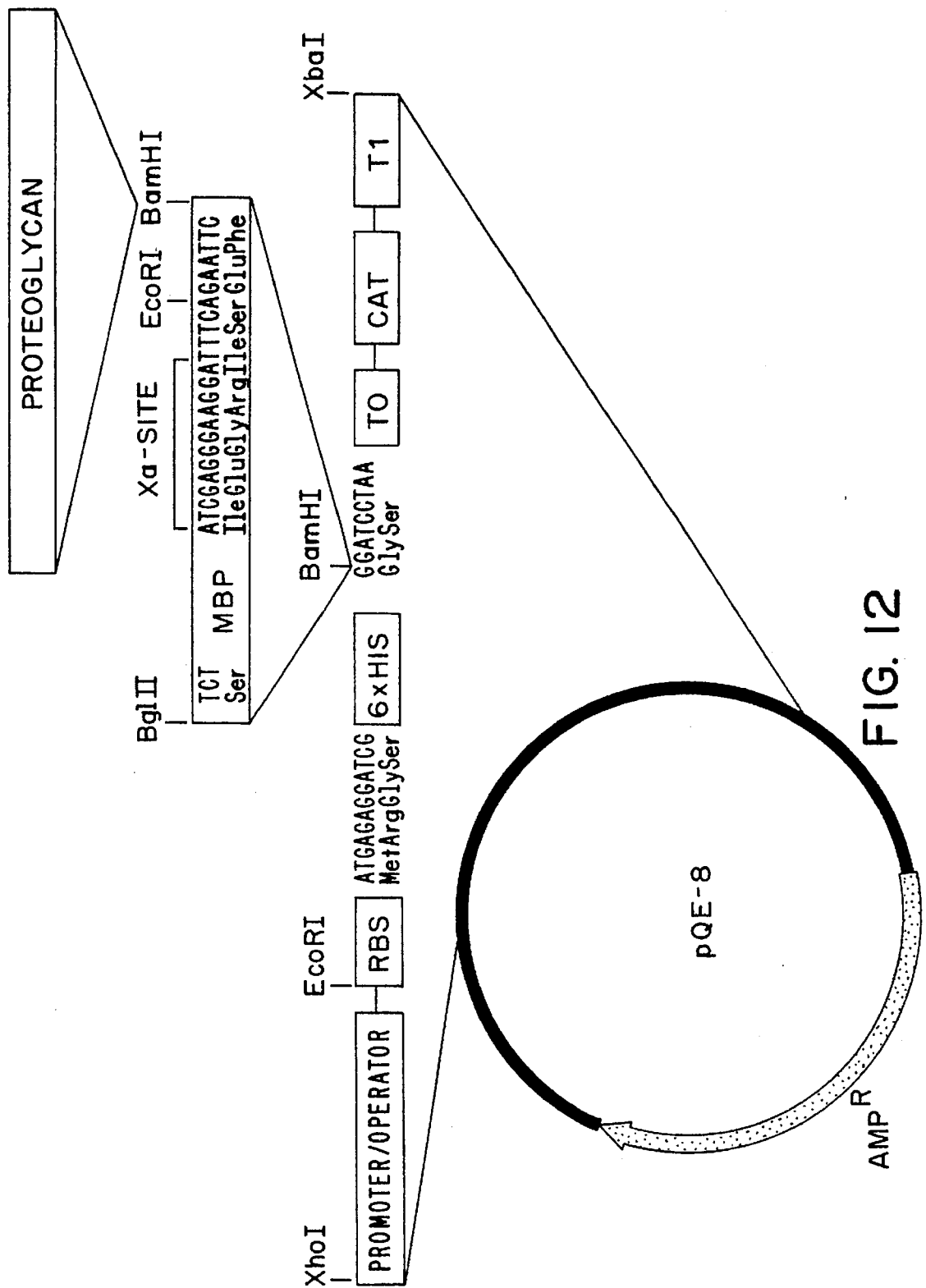

(FIG. 12). BamHI fragments coding for the core proteins of human biglycan, decorin or fibromodulin were subsequently cloned into the resulting single BamHI site in pQE-8/MBP (FIG. 12).

The histidine affinity tag allowed the purification of the fusion proteins to >95% purity in a single purification step that employs a Ni-metal-chelate affinity column (Hochuli et al., 1987).

Biglycan, decorin, and fibromodulin were prepared according to the instructions of Qiagen (Chatsworth, Calif.). Briefly, recombinant bacteria were grown in LB medium containing ampicillin (100 µg/ml) and kanamycin (25 µg/ml) at 37° C. to a density of $OD_{600}$ ~0.6 to 0.8. IPTG was then added to a final concentration of 2 mM and protein expression was allowed to proceed for 3 h. The bacteria were then collected by centrifugation (5000×g, 15 min) and lysed for 45 to 60 minutes in buffer A (0.1M $NaHPO_4$, 0.01M Tris, 6M guanidinium-HCl, pH 8.0). The lysates were centrifuged for 20 min at 20,000×g. Imidazole was added to the supernatants to a final concentration of 10 mM and the mixtures were loaded on Ni-NTA columns. The columns were washed with several column volumes of buffer B (0.1M $NaHPO_4$, 0.01M Tris, 8M urea, pH 8.0) and was eluted with buffer C (buffer B adjusted to pH 5.9). Protein-containing fractions were adjusted to pH 8 by adding 1M Tris-HCl in 8M urea. After reduction of the proteins with dithiothreitol and carboxymethylation with iodoacetamide (Charbonneau, 1989), the proteins were separated from the reagents, and buffers exchanged for the respective binding buffers by gel filtration using PD-10 columns (Pharmacia LKB Biotechnology).

Figure 13:
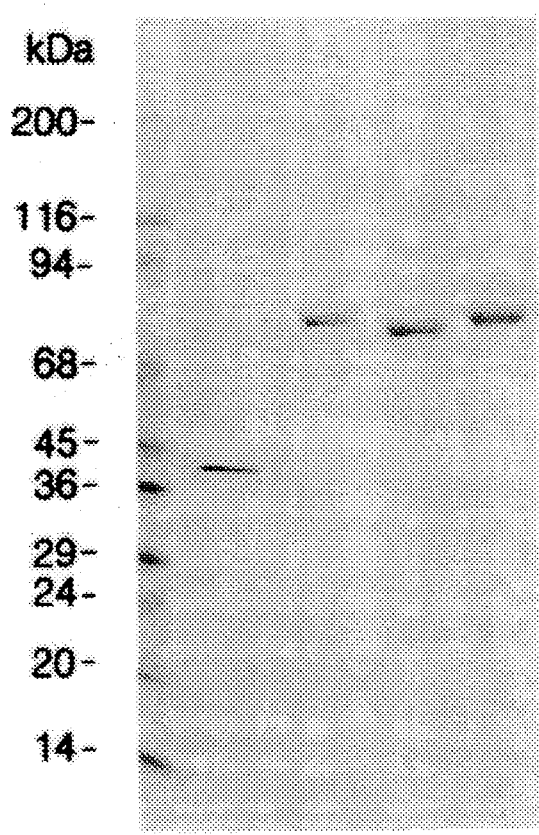
FIG. 13 shows the analyses by gel electrophoresis of purified recombinant proteoglycan core fusion proteins. Each purified protein (1 μg/well) was loaded on a 4–20% $NaDodSO_4$-polyacrylamide gel. After electrophoresis under non-reducing conditions, the gel was stained with Coomassie blue R-250. A=maltose binding protein; B=MBP-biglycan; C=MBP-decorin; D=MBP-fibromodulin. The sizes (kDa) of molecular weight marker proteins are indicated.

The purified MBP-fusion proteins displayed electrophoretic mobilities in SDS-PAGE compatible with the predicted amino acid sequences (FIG. 13). These proteins were relatively soluble in physiological buffers, although some precipitation occurred during prolonged storage at 4° C.

EXAMPLE IX

PROTEIN IODINATION

The bacterially expressed fusion proteins were iodinated using IODO-GEN according to the manufacturer's instructions (Pierce Chemical Co.). Briefly, 50 µl of an IODO-GEN solution (1 mg/25 ml $CHCl_3$) were dried to the bottom of a borosilicate glass tube. Protein (10–20 µg) dissolved in iodination buffer (0.1M $NaP_i$, 1 mM EGTA, 150 mM NaCl, pH 7.4) and carrier-free $Na^{125}I$ were added to the tube. After incubation for 12 minutes at room temperature, 200 µl of iodination buffer and the mixture were loaded into a PD-10 column for radiochemical purification of the labeled protein. The specific activities and radiochemical purities of the labeled fusion proteins were calculated by determination of the picric acid precipitable radioactive protein fraction in the labeling mixture before and after the purification step. The specific activities ranged from 2300 to 2800 Ci/mmol, with radiochemical purities greater than 95%. TGF-β1, 2 AND 3 (1–5 µg) were labeled as described above using 0.25M $NaP_i$, 2M urea, pH 7.4, as iodination buffer.

EXAMPLE X

EQUILIBRIUM BINDING EXPERIMENTS

Solid-phase binding assays were performed incubating radiolabeled MBP-proteoglycan fusion proteins in microtiter wells coated with increasing amounts of TGF-β1.

Immulon-2 microtiter wells (Dynatech; Chantilly, Va.) were coated with TGF-β1 (75 µl, 1 µg/ml) or other proteins dissolved in 0.1M bicarbonate buffer, pH 9.5, overnight at 4° C. The coated wells were then flicked dry and incubated with 200 µl of binding buffer (50 mM Tris-HCl, pH 7.4, 150 mM NaCl, 2% BSA, 0.05% Tween-20, 0.01% $NAN_3$) for 3 hours at 37° C. to block nonspecific binding sites. Plates were either used immediately or stored for future use at −20° C. for up to 2 weeks. For binding assays, the blocked wells were washed once then labeled and unlabeled proteins were added in a total volume of 100 µl binding buffer and incubated for 6 hours at 37° C. if not indicated otherwise. After that, the well contents were removed by aspiration and the wells were washed three times with ice-cold binding buffer. Binding to the surface-immobilized proteins was determined by counting the entire wells in a gamma counter.

Non-specific binding to the wells was less than 5% of the total radioactivity added. The coating efficiency for TGF-β1 was 58.7±0.5% (n=3), giving approximately 44 ng of TGF-β1 per well. The coating efficiency was calculated by adding a small amount of $^{125}I$-labeled TGF-β1 to the coating solution and determining the surface-associated radioactivity after the overnight incubation period and the subsequent washing step. All experiments were performed in duplicate or triplicate.

Figure 14:
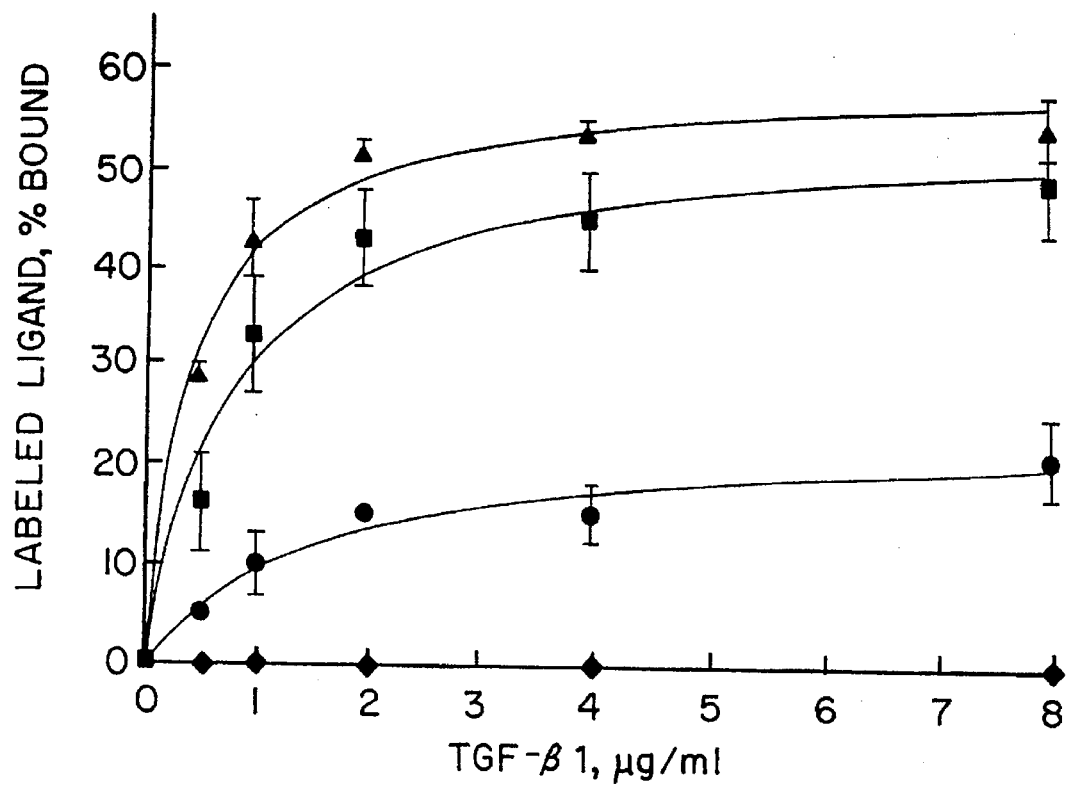
FIG. 14 shows the binding of radiolabeled proteoglycan fusion proteins and MBP to microtiter wells coated with TGF-β1. TGF-β1 was used in the indicated concentrations (75 μl/well) to coat microtiter wells. The wells were incubated with $^{125}$I-labeled MBP-biglycan (■), MBP-decorin (●), MBP-fibromodulin (▲) or MBP (♦). Constant amounts (~50,000 cpm/well, specific activities 2300–2800 Cl/mmol) of the labeled proteins were added to the TGF-β1-coated wells (total volume 100 μl). After incubation for 6 hours at 37° C., the wells were washed four times. TGF-β1-binding was determined by counting the entire wells in a gamma counter and is expressed (±S.D.) as percent of the total amount of labeled proteins added to the wells.

Radiolabeled MBP-biglycan (MBP-BG), MBP-decorin (MBP-DEC) and MBP-fibromodulin (MBP-FM) bound to TGF-β1-coated wells in a concentration-dependent manner, displaying maximum binding of 50%, 20%, and 55%, respectively (FIG. 14). Radiolabeled MBP alone did not bind to the TGF-β1-coated wells.

Figure 15:
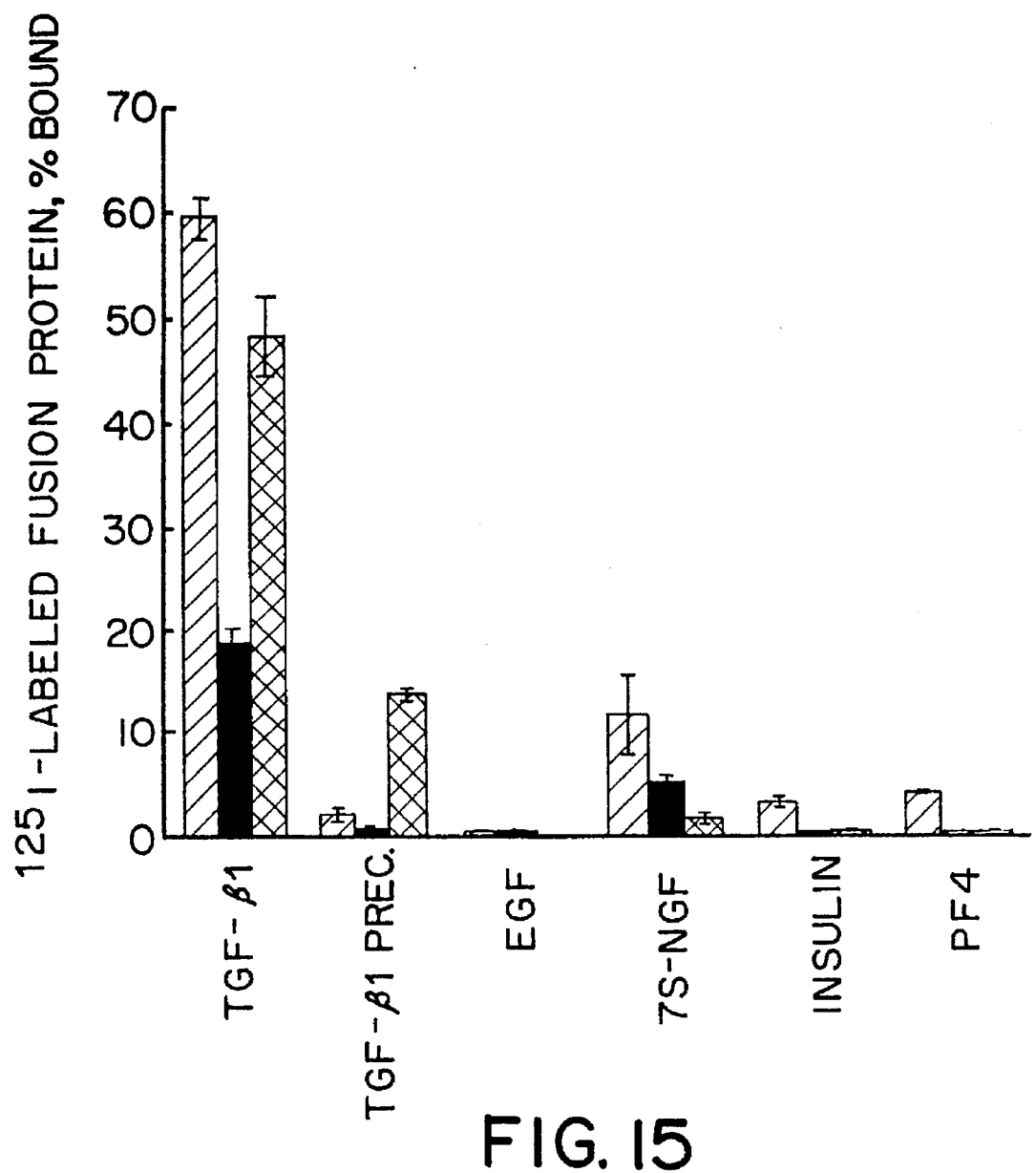
FIG. 15 shows the specificity of proteoglycan core protein binding to TGF-β1. Microtiter wells were coated with the indicated proteins (75 μl/well, 3 μg/ml). $^{125}$I-MBP-biglycan (hatched bars), $^{125}$I-MBP-decorin (solid bars) or $^{125}$I-MBP-fibromodulin (cross-hatched bars) were added to the wells (total volume 100 μl). After incubation for 6 hours at 37° C., the wells were washed three times and counted in a gamma counter. Binding (±S.D.) is expressed as percent of the total amount of labeled proteins added to the wells.

The binding of the radiolabeled fusion proteins was specific for TGF-β, since little to no binding was observed to immobilized NGF, EGF, insulin or platelet factor 4. MBP-FM bound slightly to immobilized TGF-β1 precursor protein, but MBP-BG and MBP-DEC did not (FIG. 15).

Figure 16:
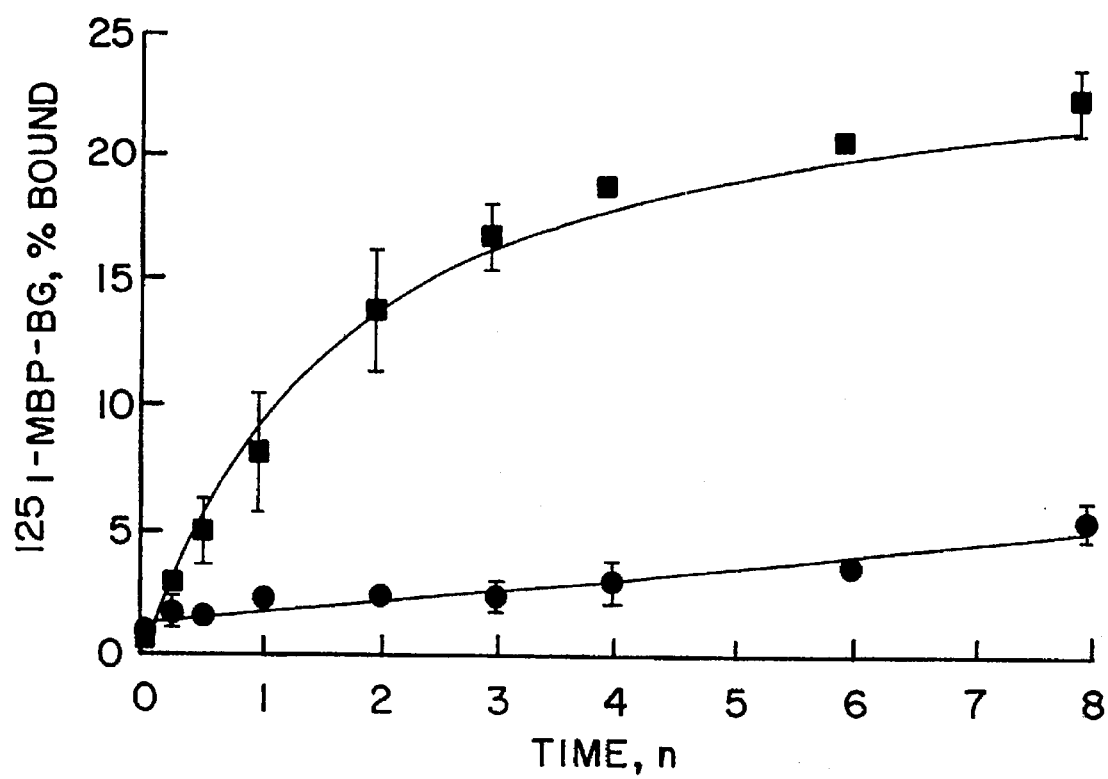
FIG. 16 shows the time-course of MBP-biglycan binding to TGF-β1. $^{125}$I-MBP-biglycan was added to TGF-β1 coated wells (75 μl, 1 μg/ml) at 4° C. (●) or 37° C. (■), respectively. After the indicated time-periods, the wells were washed three times and counted in a gamma counter. Binding (±S.D.) is expressed as percent of the total amount of $^{125}$I-MBP-biglycan added.

Since the biglycan fusion protein, MBP-biglycan, showed high binding activity toward TGF-β1, it was used to characterize further the proteoglycan-TGF-β1 interactions. The binding of MBP-BG to TGF-β1 was time- and temperature-dependent (FIG. 16). Binding increased rapidly at 37° C. but very slowly at 4° C., reaching at 4° C. only about 20% of the maximum binding seen at 37° C.

Unlabeled MBP-BG competed for the binding of $^{125}I$-labeled MBP-BG to TGF-β1 in a concentration-dependent manner (FIG. 17A). MBP-DEC and MBP-FM competed for the binding of labeled MBP-BG to TGF-β1. They were about equally effective competitors as MBP-BG, yielding half-maximal inhibitory concentrations of about 30 to 40 nM. MBP was inactive. When purified bovine proteoglycans were used as competitors, biglycan and decorin were found to be less potent than fibromodulin; the half-maximal inhibitory concentrations were 150, 200 and 10 nM, respectively.

Data from the assays shown in FIG. 17A were analyzed using the LIGAND computer program (Munson and Rodbard, 1980) to calculate dissociation constants ($K_d$) and maximal binding site concentrations ($B_{max}$) for the interaction of the proteoglycan fusion proteins with TGF-β1. Best results were obtained for two-site binding models with $K_d$ values ranging from 1 to 17 nM for high affinity binding sites and 47 to 200 nM for low affinity binding sites, respectively. The $B_{max}$ values were in the range of $10^{-13}$ moles per well for the high affinity binding sites and $1.6 \times 10^{-12}$ moles per well for the low affinity binding sites, respectively. Given a TGF-β1 coating concentration of 1 µg/ml, a coating volume of 75 µl and a coated efficiency of about 60%, these values indicate a molar ratio between proteoglycan fusion protein and TGF-β1 of one to ten for the high affinity binding site and one to one for the low affinity binding site, respectively. Proteoglycans were also tested for their ability to bind TGF-β2 and TGF-β3, the other known mammalian isoforms of TGF-β. Binding of TGF-β1, 2, and 3 to immobilized MBP-biglycan was inhibited by all three fusion proteins and all three intact proteoglycans (FIG. 18). TGF-β3 binding to MBP-BG was more effectively inhibited by decorin and biglycan than fibromodulin.

Solid-phase radioligand binding studies showed that recombinant fusion proteins containing the core protein sequences of human biglycan, decorin and fibromodulin compete for binding of labeled MBP-biglycan to TGF-β1 with similar affinities, indicating that functionally highly conserved regions of the core proteins are involved in the binding to TGF-β. The fact that bacterially produced recombinant proteoglycan core proteins had similar activities to recombinant decorin produced by mammalian cells (Yamaguchi et al., 1990) and tissue-derived proteoglycans definitively established the presence of the TGF-β binding activity in the core proteins of these proteoglycans.

EXAMPLE XI

CELL BINDING EXPERIMENTS

The ability of the proteoglycan fusion proteins to compete for TGF-β1 binding to cells was tested in cell-binding experiments. Cell binding experiments were performed according to Massagué (1987). Briefly, subconfluent monolayers of MvLu or HepG2 cells (ATCC Accession Nos. CCL 64 and HB 8065, respectively; Rockville, Md.) in 48- or 24-well cell culture dishes (Costar; Cambridge, Mass.) maintained in DMEM containing 10% FCS were used in binding experiments. Cells were incubated with labeled TGF-β1 in the presence or absence of unlabeled TGF-β1 or proteoglycan fusion proteins. The cells were washed twice with ice-cold binding buffer (128 mM NaCl, 5 mM KCl, 5 mM MgSO$_4$, 1.2 mM CaCl$_2$, 50 mM HEPES, pH 7.5, 2 mg/ml BSA) and then incubated with cell binding buffer for 30 minutes at 4° C. to remove endogenous receptor-associated TGF-β. Samples containing labeled and unlabeled proteins were added to the wells in a total volume of 100 μl for 48-well or 200 μl for 24-well dishes and were incubated at 4° C. with gentle agitation on a rotary platform. After incubation for 4 hours, the cells were washed three times with binding buffer. One-hundred microliters (200 μl for 24-well dishes) of solubilization buffer (25 mM HEPES, pH 7.5, 10% glycerol, 1% Triton X-100, 1 mg/ml BSA) were added to each well and incubated for 30 minutes at 4° C. Cell-associated radioactivity from triplicate samples was determined by counting a portion of the solubilized cells in a gamma counter.

Figure 19B:
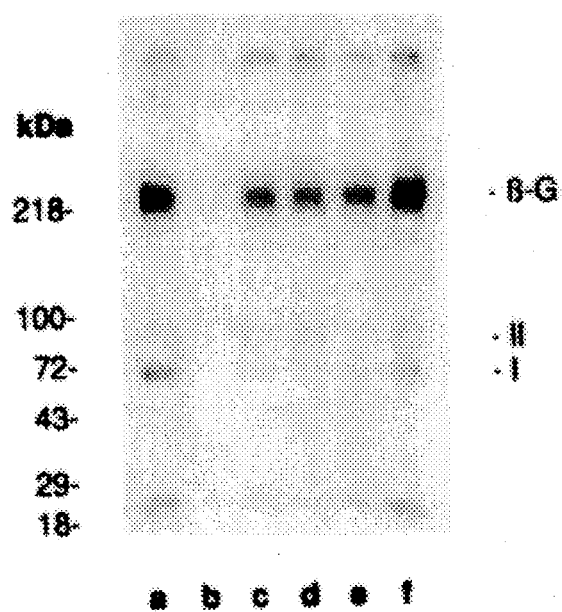
FIGS. 19A and 19B show the competition for the binding of labeled TGF-β1 to MvLu cells by proteoglycan fusion proteins.
Figure 19A:
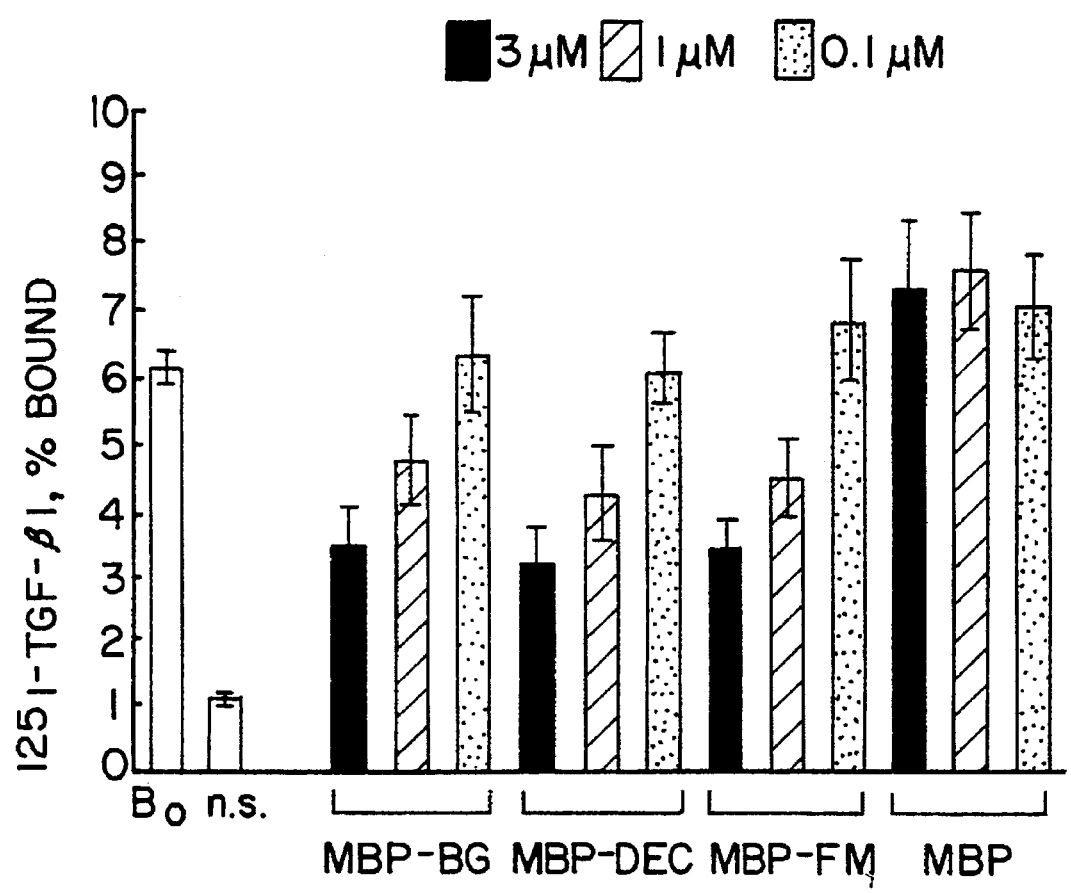

Whereas unlabeled TGF-β1 competed effectively for the binding of labeled TGF-β1 to all three types of TGF-β receptors, much higher concentrations of the proteoglycan fusion proteins were needed to compete for TGF-β1 binding to these cells (FIG. 19A). Half-maximal competition was achieved by fusion protein concentrations averaging about 3 μM.

EXAMPLE XII

CROSS-LINKING OF TGF-β TO RECEPTORS

For receptor cross-linking, cells were grown in 24-well culture dishes and were processed as described above. After incubation with labeled and unlabeled ligands, the cells were washed once with binding buffer and three times with binding buffer without BSA. Then 100 μl of binding buffer (without BSA) containing disuccinimidyl suberate (final concentration 0.2 mM) were added, and the cells were incubated for 15 min at 4° C. After the cross-linking reaction, the cells were lysed in 100 μl of solubilization buffer (125mMNaCl, 10 mM Tris, pH 7, 1 mM EDTA, 1% Triton X-100, 10 μg/ml leupeptin, 10 μg/ml antipain, 50 mg/ml aprotinin, 100 μg/ml benzamidine-HCl, 10 μg/ml pepstatin). The lysates were mixed with sample buffer and analyzed by SDS-PAGE under reducing conditions using precast 4–12% Novex gels. After electrophoresis the gels were dried and exposed to XAR-100 x-ray film for several days at −70° C.

Cross-linking experiments revealed that TGF-β1 binding to the type I and type III receptors was affected more by all three proteoglycan fusion proteins than binding to the type II receptors, which was essentially unchanged (FIG. 19B). Laser densitometry analyses of the respective autoradiograms showed that the binding of labeled TGF-β1 to type I and III receptors was decreased by approximately 25% or 50%, respectively, at the proteoglycan concentration used.

Competition was most effective for TGF-β binding to the type I and type III TGF-β receptors, perhaps because these receptors have a lower affinity for TGF-β than does the type II receptor. While the affinities of the proteoglycans for the TGF-β are much lower than those of any of the receptors, all of the proteoglycans are abundant in tissues potentially making up in concentration what they may lack in affinity. Moreover, the experimental conditions used in the cell binding experiments do not favor the binding of TGF-β to proteoglycans.

Although the invention has been described with reference to the presently-preferred embodiments, it should be understood that various modifications can be made without departing from the spirit of the invention. Accordingly, the invention is limited only by the following claims.

---

We claim:

1. A method for reducing scarring associated with a dermal wound, comprising the step of administering fibromodulin to the site of said wound in an amount effective to reduce said scarring.

2. A method according to claim 1, wherein said amount of fibromodulin is effective to prevent said scarring.

* * * * *

UNITED STATES PATENT AND TRADEMARK OFFICE
CERTIFICATE OF CORRECTION

PATENT NO. : 5,654,270
DATED : Aug. 5, 1997
INVENTOR(S) : Ruoslahti et al.

It is certified that error appears in the above-indentified patent and that said Letters Patent is hereby corrected as shown below:

Abstract: Line 4, please delete "including" and replace with --includes--.

Column 1, line 38, please delete "GM-CSP" and replace with --GM-CSF--.

Column 3, line 15, please delete "TGF-B" and replace with --TGF-$\beta$ --.

Column 3, line 35, please delete "alanic" and replace with -- alanine --.

Column 3, line 46, please delete "2A - 12B" and replace with --2A - 2B--.

Column 4, line 61, please delete "SDS-PAGE.FIG.7B" and replace with -- SDS-PAGE. FIG.7B--.

Column 5, line 50, please delete "Cl/mmol)" and replace with --Ci/mmol)-- (C&F error).

Column 6, line 22, please delete "Cl/mmol)" and replace with --Ci/mmol)-- (C&F error).

UNITED STATES PATENT AND TRADEMARK OFFICE
CERTIFICATE OF CORRECTION

PATENT NO. : 5,654,270
DATED : Aug 5, 1997
INVENTOR(S) : Ruoslahti et al.

It is certified that error appears in the above-indentified patent and that said Letters Patent is hereby corrected as shown below:

Column 8, line 22, please delete "TGF-ββs." and replace with --TGF-βs.--

Column 9, line 58, please delete "TGF-B" and replace with --TGF-β.--

Column 11, line 23, please delete "3-5x105 cells" and replace with -- 3-5 x $10^5$ cells--.

Column 13, line 7, please delete "Plow" and replace with --Flow--.

Column 13, line 10, please delete "0-5mM" and replace with --0.5mM--.

Column 13, line 29, please delete "alaninc-mutated" and replace with --alanine-mutated--.

Column 13, line 57, please delete "Chromatoqraphy" and replace with --Chromatography--.

Column 13, line 61, please delete "TGF-B1" and replace with --TGF-β1"--.

Column 15, line 18, please delete "FIGS.3A-13B:" and replace with --FIGS.3A-3B:--

UNITED STATES PATENT AND TRADEMARK OFFICE
CERTIFICATE OF CORRECTION

PATENT NO. : 5,654,270
DATED : Aug. 5, 1997
INVENTOR(S) : Ruoslahti et al.

It is certified that error appears in the above-indentified patent and that said Letters Patent is hereby corrected as shown below:

Column 15, line 33, please delete "0.1MTris/Cl," and replace with -- 0.1MTris/HCl,--.

Column 20, line 11, please delete "Massoh's" and replace with --Masson's--.

Column 24, line 21, please delete "(125mMNaCl," and replace with -- (125mM NaCl,--.

Signed and Sealed this

Twenty-third Day of February, 1999

Q. TODD DICKINSON

*Attest:*

*Attesting Officer*  Acting Commissioner of Patents and Trademarks